United States Patent
Li et al.

(10) Patent No.: US 9,670,213 B2
(45) Date of Patent: Jun. 6, 2017

(54) PTERIDINE KETONE DERIVATIVE AND APPLICATIONS THEREOF AS EGFR, BLK, AND FLT3 INHIBITOR

(71) Applicant: EAST CHINA UNIVERSITY OF SCIENCE AND TECHNOLOGY, Shanghai (CN)

(72) Inventors: Honglin Li, Shanghai (CN); Yufang Xu, Shanghai (CN); Zhenjiang Zhao, Shanghai (CN); Xiaofeng Liu, Shanghai (CN); Wei Zhou, Shanghai (CN); Fang Bai, Shanghai (CN); Mengzhu Xue, Shanghai (CN); Lei Zhang, Shanghai (CN); Youli Zhang, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 0 days.

(21) Appl. No.: 14/400,508

(22) PCT Filed: Apr. 2, 2013

(86) PCT No.: PCT/CN2013/073612
§ 371 (c)(1),
(2) Date: Nov. 11, 2014

(87) PCT Pub. No.: WO2013/170671
PCT Pub. Date: Nov. 21, 2013

(65) Prior Publication Data
US 2015/0126508 A1    May 7, 2015

(30) Foreign Application Priority Data
May 14, 2012  (CN) .......................... 2012 1 0148939
Nov. 23, 2012  (CN) .......................... 2012 1 0484897

(51) Int. Cl.
*C07D 401/12* (2006.01)
*C07D 475/04* (2006.01)
*C07D 487/02* (2006.01)
*C07D 475/00* (2006.01)
*C07D 239/50* (2006.01)

(52) U.S. Cl.
CPC ......... *C07D 475/00* (2013.01); *C07D 239/50* (2013.01)

(58) Field of Classification Search
CPC ... C07D 401/12; C07D 475/04; C07D 487/02
See application file for complete search history.

(56) References Cited

U.S. PATENT DOCUMENTS

2006/0047118 A1    3/2006  Stadtmueller et al.

FOREIGN PATENT DOCUMENTS

| CN | 1373763 A | 10/2002 |
|---|---|---|
| WO | WO 2004/065378 | 8/2004 |
| WO | WO 2006091737 | * 8/2006 |

OTHER PUBLICATIONS

PCT International Search Report and Written Opinion dated Jul. 11, 2013 issued in PCT/CN2013/073612 (WO/2013/170671).
Ott et al. (1974) "Zur Synthese des 4-Amino-7-oxo-7, 8-dihydropteridin-$N$-8-$\beta$-D-ribofuranosids-ein strukturanaloges Nucleosid des Adenosins" *Chem. Ber.* 107:339-361.

* cited by examiner

*Primary Examiner* — Bruck Kifle
(74) *Attorney, Agent, or Firm* — Tom Hunter; Weaver Austin Villeneuve & Sampson LLP

(57) ABSTRACT

Provided are a pteridine ketone derivative used as an EGFR, BLK, and FLT3 inhibitor and applications thereof. Specifically, provided are a compound of the following formula I, a pharmaceutical composition containing the compound of the formula I, and use of compound in preparing medicine for treating diseases mediated by EGFR, BLK, or FLT3 or inhibiting EGFR, BLK, and FLT3.

9 Claims, No Drawings

PTERIDINE KETONE DERIVATIVE AND APPLICATIONS THEREOF AS EGFR, BLK, AND FLT3 INHIBITOR

CROSS-REFERENCE TO RELATED APPLICATIONS

This application is a 371 National Phase of PCT/CN2013/073612, filed on Apr. 2, 2013, which claims priority to CN 201210484897.0 filed on Nov. 23, 2012, and to CN 201210148939.3, filed on May 14, 2012.

TECHNICAL FIELD

The present invention relates to the synthesis of pteridine ketone compounds and uses thereof in the field of medical chemistry and pharmacotherapeutics. Particularly, the invention relates to the use of pteridine ketone compounds with various substituents as EGFR, BLK, FLT3 inhibitors, especially the use in preparing drugs for treating tumor-related diseases.

BACKGROUND

Malignant tumor is a cytopathy, characterized in that the normal cell division is out of control, resulting in the immoderate cell-differentiation and proliferation, invasion into local tissues and metastasis. Malignant tumors have become common diseases seriously detrimental to the life and health of human. According to the incomplete statistic data, there are about 20 million new cases per year in the world. Therefore, at present, it is the most challenging and significant area in life science to research and develop antitumor drugs.

Generally, traditional antitumor drugs are cytotoxic drugs, which have disadvantages, such as inevitable toxic and side effects, poor selectivity and resistance, etc. Various basic life processes in malignant tumor cells, such as signal transduction, regulation on cell-cycle, angiogenesis and the like, have been gradually demonstrated with the rapid progress in life science. It is an important aspect in the research of antitumor drugs to develop antitumor drugs with excellent therapeutic efficacy and low side effects by using certain key enzymes, which are relevant to the proliferation of tumor cells in signal transduction paths, as targets for drug screening. Protein tyrosine kinase is a kind of protein for catalyzing the transfer of γ-phosphate from ATP to certain amino acid residue of a protein, which plays an important role in the intracellular signal transduction path, and regulates a series of physiological processes, such as cell growth, differentiation and death. According to the information in prior art, over 50% of oncogenes and the products thereof possess protein tyrosine kinase activities, the aberrant expression of which will result in the disorder of life-cycle of cells, and, in turn, the formation of tumor. Additionally, the aberrant expression of tyrosine kinase is closely relevant to tumor metastasis and chemoresistance.

Epidermal growth factor receptor tyrosine kinase (EGFR) can modulate multiple signal transduction paths, transfer the extracellular signal into cell, and play an important role in regulating the proliferation, differentiation and apoptosis of normal cells and tumor cells (Cell, 2000, 100, 113-127). Therefore, the purpose for treating tumors can be achieved by selectively inhibiting the signal transduction path modulated by EGFR, thereby providing a feasible way for targeting-treatment of tumors. The drugs with EGFR as the target, such as Gefitinib, Erlotinib and Laptinib, have been marketed, for treating non-small cell lung cancer and breast cancer. However, according to clinical experience, resistance will occur in most of non-small cell lung cancer patients after being repeatedly treated by using Gefitinib or Erlotinib, wherein 50% of resistance cases are relevant to the mutation of one amino acid in EGFR kinase domain (threonine residue at position 790 is mutated to methionine, T790M) (The New England Journal of Medicine, 2005, 352, 786-792). For overcoming the T790M-relevant resistance, a series of irreversible ATP competitive inhibitors, such as CI-1033, BIBW2992, HKI-272, PF00299804 etc., have been clinically studied. The irreversible inhibitors have one Michael receptor fragment capable of forming a covalent bond with one conservative amino acid (Cys797) in ATP binding site of EGFR, thereby obtaining stronger EGFR-binding affinity, compared with reversible inhibitor (Journal of Medicinal Chemistry, 2009, 52, 1231-1246). However, the results from clinical experiments for the irreversible inhibitors said above are not ideal, due to the toxicity from off-target effects, side effects from low selectivity, and insufficient drug concentration in a patient in vivo, etc (Nature, 2009, 462, 1070-1074). Therefore, the development of novel irreversible EGFR inhibitors will have great clinical significance and application prospects.

B lymphocyte tyrosine kinase (BLK) belongs to a non-receptor tyrosine kinase, and is classified into Src family as c-Src, Fyn, Lck, c-Yes, Fgr, Hck, Lyn, etc. BLK is mainly expressed in B lymphocyte line, and during the whole process of B lymphocyte development, except for plasma cell phase, BLK is expressed. BLK involves in downstream signal transduction of B lymphocyte receptor (BCR) (Molecular Biology Reports, 2011, 38, 4445-4453), and affects pre-B lymphocyte receptor-related functions (Journal of Experimental Medicine, 2003, 198, 1863-1873), thereby affects differentiation and proliferation of B lymphocyte. Constitutively activated BLK expressed in Murine B cell line, T cell lines will lead to the development of B-cell lymphoma, T-cell lymphoma respectively (Proceedings of the National Academy of Sciences, 1998, 95, 7351-7356). More importantly, the ectopic expression of BLK is present in human cutaneous T-cell lymphoma (CTCL) (Blood, 2009, 113, 5896-5904), suggesting that BLK can be used as a potential target for anticancer drug. In addition, BLK gene polymorphism is closely related to pathogenesis of systemic lupus erythematosus (SLE), rheumatoid arthritis (RA) and other autoimmune diseases (The New England Journal of Medicine, 2008, 358, 900-909), and induction of apoptosis of B-cells may be an effective treatment for the above diseases (Nat Reviews Immunology, 2006, 6, 394-403).

FMS-like tyrosine kinase 3 (FLT3), which belongs to type III receptor tyrosine kinase family, plays an important role in the proliferation, differentiation and apoptosis of hematopoietic cell (Oncogene, 1993, 8, 815-822). Upon binding to FLT3 ligand, FLT3 activates multiple downstream signaling pathways, including STATS, Ras/MAPK and PI3K/AKT pathway. FLT3 mutations exist in about one third of acute myeloid leukemia (AML) patients (Blood, 2002, 100, 1532-1542), including mutations in internal tandem duplication sequences of juxtamembrane domain 14 and (or) 15 exons (FLT3-ITD), and mutations of amino acid deletion or insertion in activation loop of tyrosine kinase domain (FLT3-TKD). Moreover, high expression of FLT3 can be found in acute leukemia cases (Blood, 2004, 103, 1901), and over-expression of FLT3, FLT3-ITD mutation and FLT3-TKD mutation will lead to a poor prognosis in AML patients. Thus, FLT3 has become an important target for the treatment of AML. So far, there is no FLT3 inhibitors are approved for clinical use, and clinical effects of many FLT3 inhibitors in clinical trials are not desirable yet.

Therefore, it is a hot-spot in the research and development of anti-tumor targeted drugs to improve the clinical efficacy of small molecule kinase inhibitors, and the most promising strategy is to develop multi-target inhibitors simultaneously targeting multiple kinases associated with pathogenesis of disease (tumor).

SUMMARY OF THE INVENTION

The present inventors establish a virtual screening platform for EGFR, BLK, FLT3 specific small molecule inhibitors by using computer-aided drug design. Comprehensively considering the pharmacophore and molecular docking method, the inventors screened commercial compound databases (including ACD-3D (chemical library), ACD-SC, MDDR-3D (drug activity data library) and CNPD) and found a group of candidates with potential EGFR, BLK, FLT3 inhibitory activity.

The structure of obtained candidate compounds was optimized, and a series of unreported pteridine ketone compounds were designed and synthesized, the structure of which was characterized. The activities of the compounds were tested on molecular and cell level, thereby obtaining compounds with high EGFR inhibitory activity. Among them, $IC_{50}$ values of Compound 032 are 3.67, 2.36, and 1.17 nM for inhibiting activities of $EGFR^{WT}$, $EGFR^{L858R}$, $EGFR^{T790M/858R}$ kinases, and 0.004, 0.038 μM for inhibiting the proliferation of HCC827 cell (non-small cell lung cancer cell, $EGFR^{del\ E746-A750}$), H1975 (non-small cell lung cancer cell, $EGFR^{L858R/T790M}$) cell.

The pteridine ketone compounds according to the present invention can be used as EGFR inhibitors for blocking phosphorylation of EGFR and inhibiting the growth, proliferation and differentiation of tumor cells, therefore, these compounds can be developed into novel antitumor drugs. Moreover, The pteridine ketone compounds according to the present invention possess high inhibitory activities against B lymphocyte kinase (BLK) and FMS-like tyrosine kinase 3 (FLT3), and can be used in the development of drugs for treating tumors, and immune diseases.

The pteridine ketone compounds according to the present invention have the structure of general formula I:

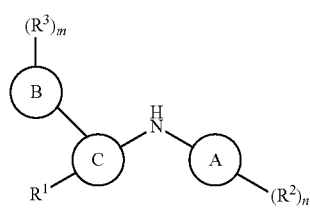

I wherein,

A and B are a benzene ring or five- or six-member heterocycle with various substituents;

C is selected from any of the following groups:

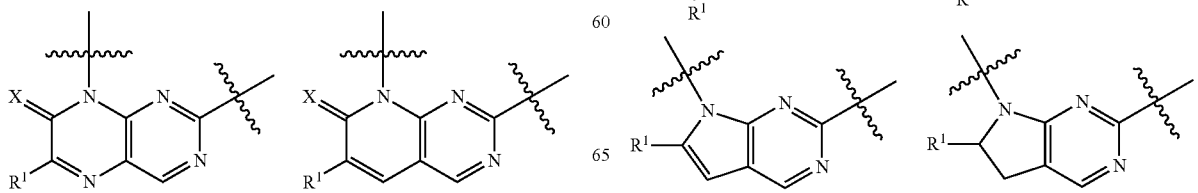

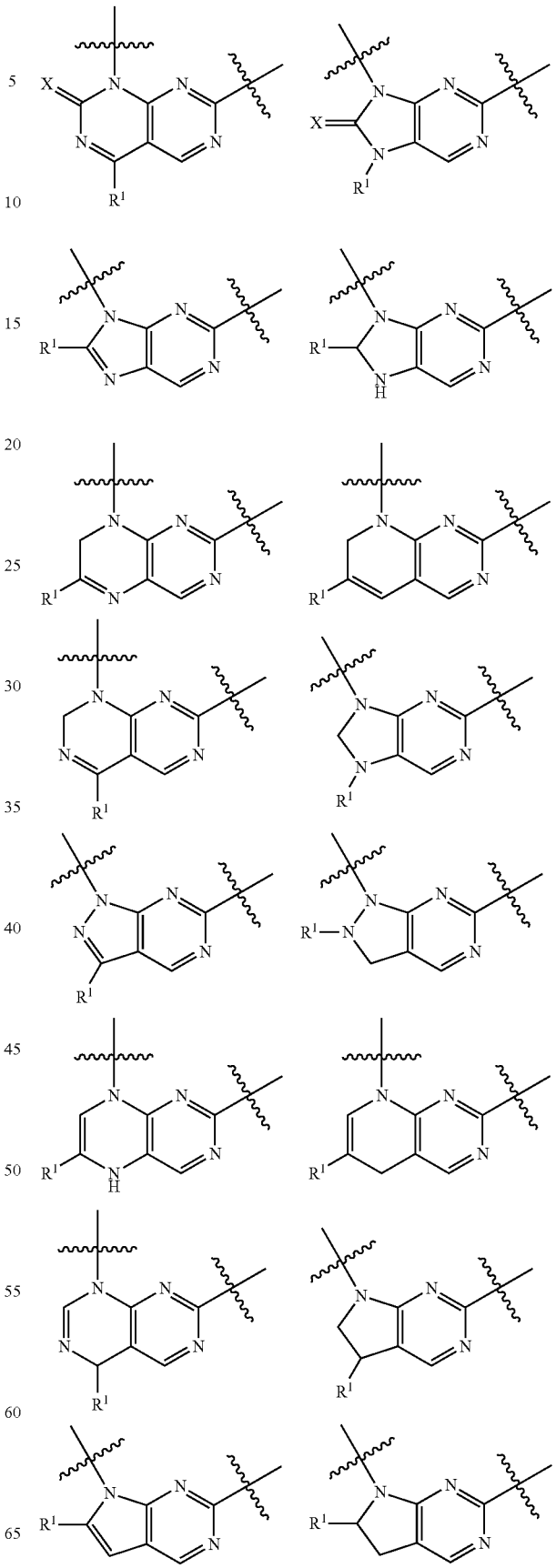

-continued

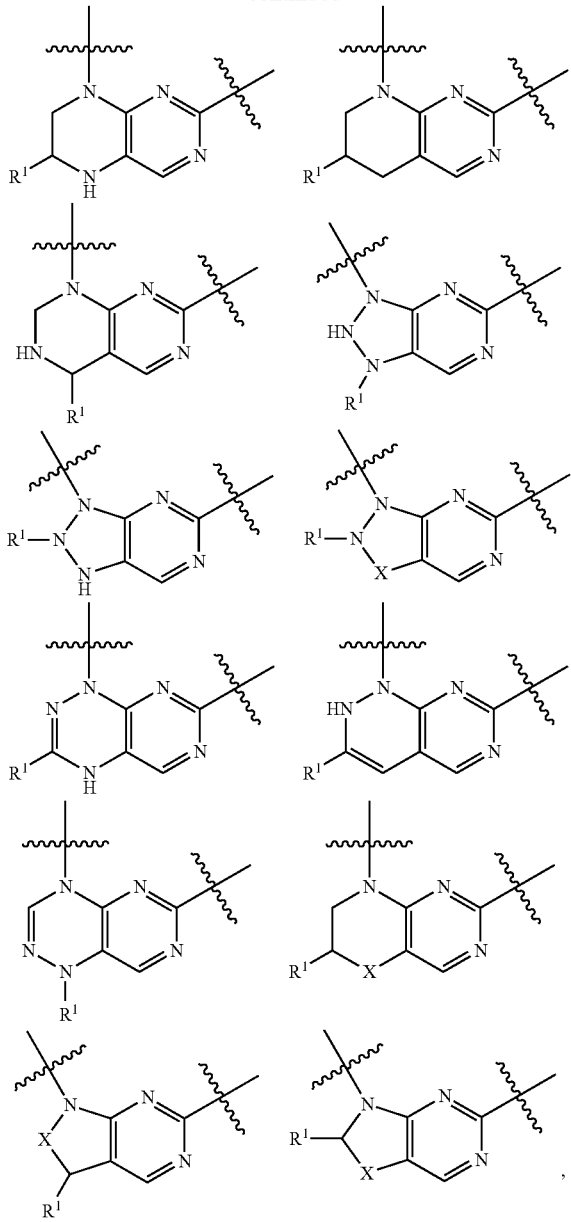

wherein X is selected from O, S and Se; $R^1$ is a hydrogen, a halogen atom, a $C_1$-$C_6$ alkoxyl (e.g., methoxyl, ethoxyl, etc.), an optionally substituted $C_1$-$C_6$ alkyl (e.g., a halogen-substituted alkyl), an optionally substituted aryl (e.g., a halogen-substituted aryl) or an optionally substituted aralkyl (e.g. an arylmethyl);

each of $R^2$ is independently selected from a hydrogen, a halogen, a $C_1$-$C_6$ alkoxyl, a hydroxyl, an optionally substituted acyloxy, an amino, an optionally substituted acylamino, an optionally substituted $C_1$-$C_6$ alkyl, CN, a sulfonate group, a sulfamoyl, a carbamoyl, a carboxyl, an optionally substituted alkoxyformyl, optionally substituted phenyl, optionally substituted N-alkylpiperazinyl, an optionally substituted morpholinyl, an optionally substituted piperidinyl, an optionally substituted pyrrolyl, optionally substituted pyrrolidinyl, —$NR_aR_b$, an optionally substituted pyridyl;

each of $R^3$ is independently selected from a hydrogen, a halogen, a $C_1$-$C_6$ alkoxyl, a hydroxyl, an optionally substituted acyloxy, an amino, an optionally substituted acylamino, an optionally substituted $C_1$-$C_6$ alkyl, CN, a sulfonate group, a sulfamoyl, a carbamoyl, a carboxyl, an optionally substituted alkoxyformyl, an optionally substituted phenyl, an optionally substituted N-alkyl piperazinyl, an optionally substituted morpholinyl, an optionally substituted piperidinyl, an optionally substituted pyrrolyl, an optionally substituted pyrrolidinyl, —$NR_aR_b$, and an optionally substituted pyridyl;

$R_a$ and $R_b$ are independently selected from an alkyl and an alkenyl; and m and n are independently selected from 0, 1, 2, 3, or 4.

In a embodiment, $R^3$ is independently selected from a hydrogen, a hydroxyl, an optionally substituted acyloxy, an optionally substituted amino, an optionally substituted acylamino, an optionally substituted $C_1$-$C_4$ alkyl, CN, a sulfonate group, a sulfamoyl, a carboxyl, an optionally substituted alkoxyformyl.

In a embodiment, C is a group of the following formula:

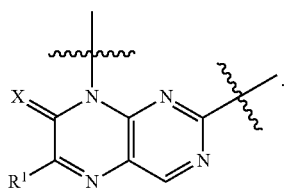

In a embodiment, $R^1$ is selected from H and an alkyl.

In a embodiment, both of A and B are optionally substituted phenyl.

In a embodiment, $R^2$ is independently selected from H, an alkoxyl, a morpholinyl, a halogen, a N-alkyl-piperazinyl, a piperidinyl, a pyrrolyl, a pyrrolidinyl, a pyridyl, —$NR_aR_b$, an acylamino and a carbamoyl ($NH_2C(O)$—), wherein, $R_a$ and $R_b$ are selected from an alkyl and an alkenyl.

In a embodiment, $R^2$ is independently selected from a 4-N-methylpiperazinyl, a N-morpholinyl, a N-piperidinyl, a N-pyrrolyl, a N-pyrrolidinyl, a N,N-diethylamino, a N,N-dimethyl-methylamine group and 4-pyridyl.

In a embodiment, $R^3$ is independently selected from a hydrogen, an amino, an acyloxy, an alkoxyl, a halogen, a hydroxyl, an alkyl, CN, a sulfonate group, an sulfamoyl, a carboxyl, a morpholinyl, a N-alkyl-piperazinyl, a piperidinyl, a pyrrolyl, a pyrrolidinyl, a pyridyl, —$NR_aR_b$, an acylamino and a carbamoyl, wherein $R_a$ and $R_b$ are selected from an alkyl and an alkenyl.

In a embodiment, $R^3$ is independently selected from an acylamino, an acyloxy and an alkoxyl.

In a embodiment, $R^3$ is independently selected from the following groups:

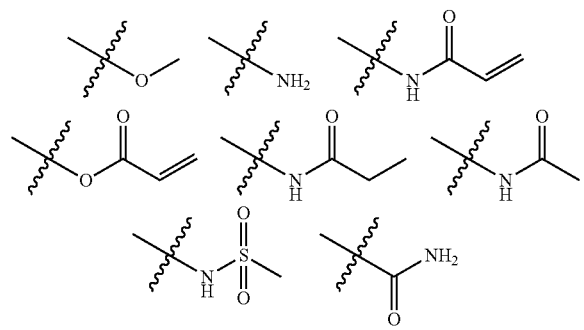

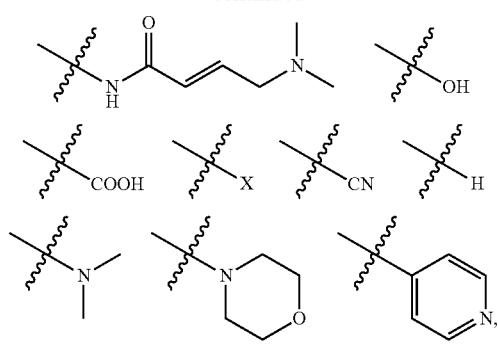

wherein X is a halogen.

In a embodiment, R³ is independently selected from the following groups:

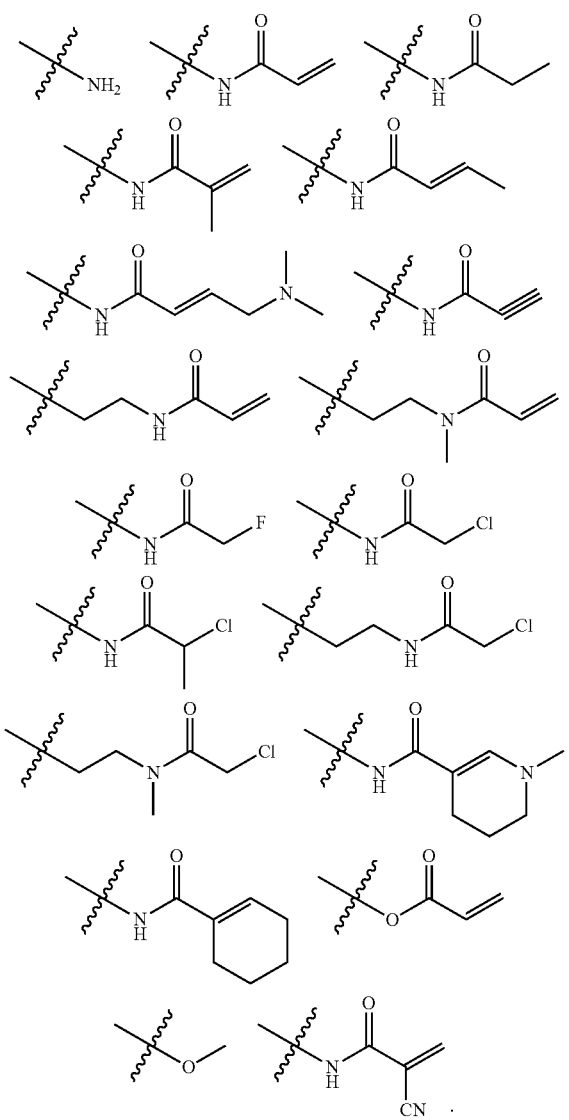

In a embodiment, R³ is selected from the following groups:

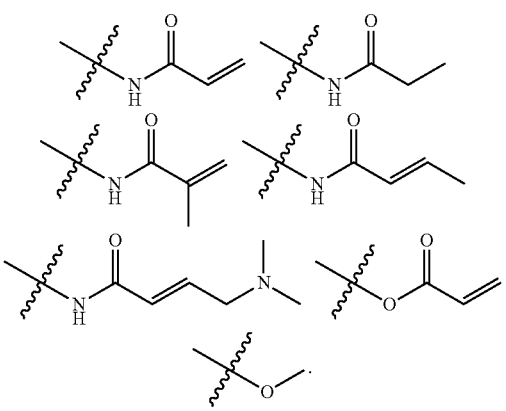

In a embodiment, m is 1 or 2.

In a embodiment, n is 1, 2, 3, or 4.

In a embodiment, in the group of C, the wavy comprising R¹ moiety is connected to C, while the other part is connected to NH.

In a preferred embodiment of the present invention, the compound has the structure of general formula II:

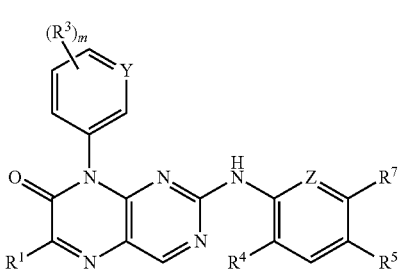

wherein,
Y is selected from N, CH;
Z is selected from N, CR⁶;
R¹ is a hydrogen, a halogen, a $C_1$-$C_6$ alkoxyl, an optionally substituted $C_1$-$C_6$ alkyl, an optionally substituted aryl, an optionally substituted aralkyl;
R³ is independently selected from a hydrogen, an amino, a hydroxyl, an optionally substituted acyloxy, an alkoxyl, a halogen, an optionally substituted alkyl, CN, a sulfonate group, a sulfamoyl, a carboxyl, a morpholinyl, a N-alkylpiperazinyl, a piperidinyl, a pyrrolyl, a pyrrolidinyl, a pyridyl, —NR$_a$R$_b$, an optionally substituted acylamino, an optionally substituted alkoxyformyl, and carbamoyl;
each of R⁴, R⁵, R⁶ and R⁷ is independently selected from a hydrogen, a halogen, a $C_1$-$C_6$ alkoxyl, a hydroxyl, an optionally substituted acyloxy, an amino, an optionally substituted acylamino, an optionally substituted $C_1$-$C_6$ alkyl, CN, a sulfonate group, a sulfamoyl, a carbamoyl, a carboxyl, an optionally substituted alkoxyformyl, an optionally substituted phenyl, an optionally substituted N-alkylpiperazinyl, an optionally substituted morpholinyl, an optionally substituted piperidinyl, an optionally substituted pyrrolyl, an optionally substituted pyrrolidinyl, —NR$_a$R$_b$, an optionally substituted pyridyl;
R$_a$ and R$_b$ are selected from an alkyl and an alkenyl; and
m is an integer from 0-3.

In a preferred embodiment of formula II, R³ is selected from an optionally substituted acyloxy, an amino, an optionally substituted acylamino, an optionally substituted $C_1$-$C_4$ alkyl, CN, a sulfonate group, a sulfamoyl, a carboxyl and an optionally substituted alkoxyformyl.

In a more preferred embodiment of the present invention, the compound has the structure of general formula III:

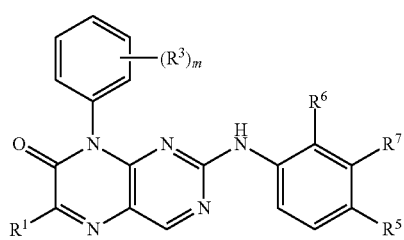

III wherein, $R^1$ is a hydrogen, a halogen, a $C_1$-$C_6$ alkoxyl, an optionally substituted $C_1$-$C_6$ alkyl, an optionally substituted aryl, an optionally substituted aralkyl;

$R^3$ is independently selected from a hydrogen, an amino, a hydroxyl, an optionally substituted acyloxy, an alkoxyl, a halogen, an optionally substituted alkyl, CN, a sulfonate group, a sulfamoyl, a carboxyl, a morpholinyl, a N-alkyl-piperazinyl, a piperidinyl, a pyrrolyl, a pyrrolidinyl, a pyridyl, —$NR_aR_b$, an optionally substituted acylamino, an optionally substituted alkoxyformyl, and carbamoyl;

each of $R^5$, $R^6$ and $R^7$ is independently selected from a hydrogen, a halogen, a $C_1$-$C_6$ alkoxyl, a hydroxyl, an optionally substituted acyloxy, an amino, an optionally substituted acylamino, an optionally substituted $C_1$-$C_6$ alkyl, CN, a sulfonate group, a sulfamoyl, a carbamoyl, a carboxyl, an optionally substituted alkoxyformyl, an optionally substituted phenyl, an optionally substituted N-alkyl-piperazinyl, an optionally substituted morpholinyl, an optionally substituted piperidinyl, an optionally substituted pyrrolyl, an optionally substituted pyrrolidinyl, —$NR_aR_b$, an optionally substituted pyridyl;

$R_a$ and $R_b$ are selected from an alkyl and an alkenyl; and m is 0, 1, 2 or 3.

In a preferred embodiment of formula III, $R^1$ is selected from H and an alkyl.

In a preferred embodiment of formula III, $R^3$ is selected from an optionally substituted acyloxy, an amino, an optionally substituted acylamino, an optionally substituted $C_1$-$C_4$ alkyl, CN, a sulfonate group, a sulfamoyl, a carboxyl and an optionally substituted alkoxyformyl;

In a preferred embodiment of formula III, $R^5$ and $R^6$ are independently selected from H, an alkoxyl, a morpholinyl, a halogen, a N-alkyl-piperazinyl, a piperidinyl, a pyrrolidinyl, —$NR_aR_b$, an acylamino and a carbamoyl ($NH_2C(O)$—), wherein $R_a$ and $R_b$ are selected from an alkyl and an alkenyl.

In a preferred embodiment of formula III, $R^5$ is selected from H, an alkoxyl, a morpholinyl, a halogen, a N-alkyl-piperazinyl, a piperidinyl, a pyrrolyl, a pyrrolidinyl, a pyridyl, —$NR_aR_b$, an acylamino and a carbamoyl ($NH_2C$(O)—), wherein $R_a$ and $R_b$ can be selected from an alkyl and an alkenyl.

In a preferred embodiment of formula III, $R^5$ is selected from H, an alkoxyl, a morpholinyl, a halogen, a N-alkyl-piperazinyl, a piperidinyl, a pyrrolyl, a pyrrolidinyl, a pyridyl, —$NR_aR_b$, an acylamino and a carbamoyl ($NH_2C$(O)—), wherein $R_a$ and $R_b$ can be selected from an alkyl and an alkenyl; $R^6$ is H.

In a preferred embodiment of formula III, $R^5$ is selected from a halogen, a 4-N-methylpiperazinyl, a N-morpholinyl, a N-piperidinyl, a N-pyrrolyl, a N-pyrrolidinyl, a N,N-diethyl-amino, a N,N-dimethylmethylamine group and 4-pyridyl.

In a preferred embodiment of formula III, $R^5$ and $R^6$ are H, and $R^7$ is an acylamino.

In a preferred embodiment of formula III, $R^3$ is independently selected from an acylamino, an acyloxy and an alkoxyl.

In a preferred embodiment of formula III, $R^3$ is independently selected from the following groups:

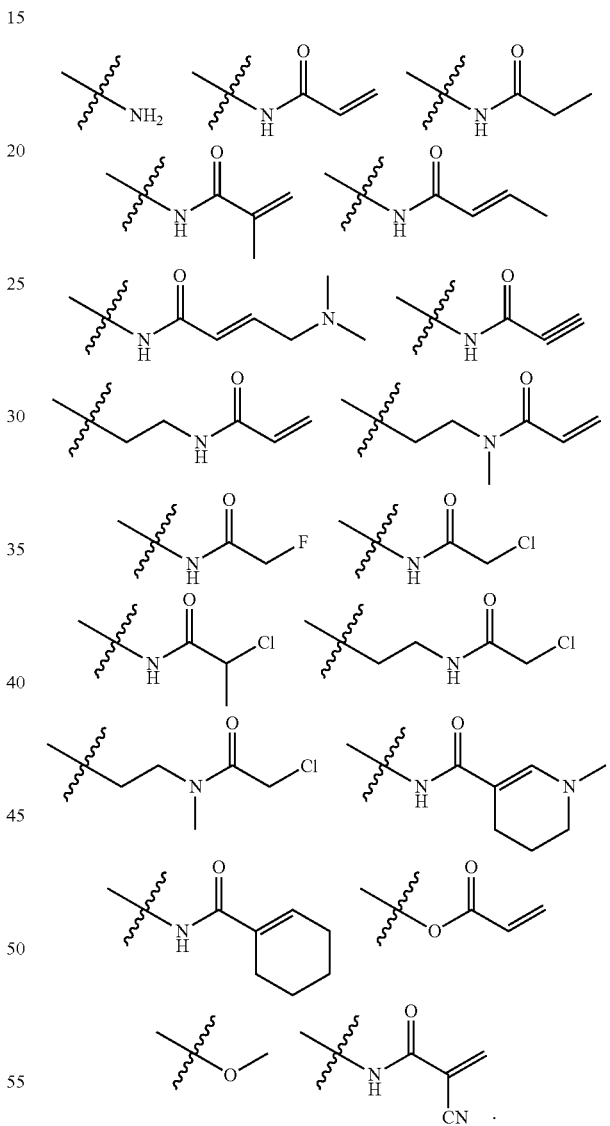

In a preferred embodiment of formula III, $R^3$ is selected from the following groups:

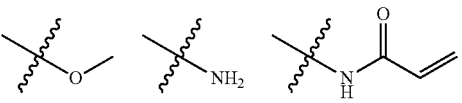

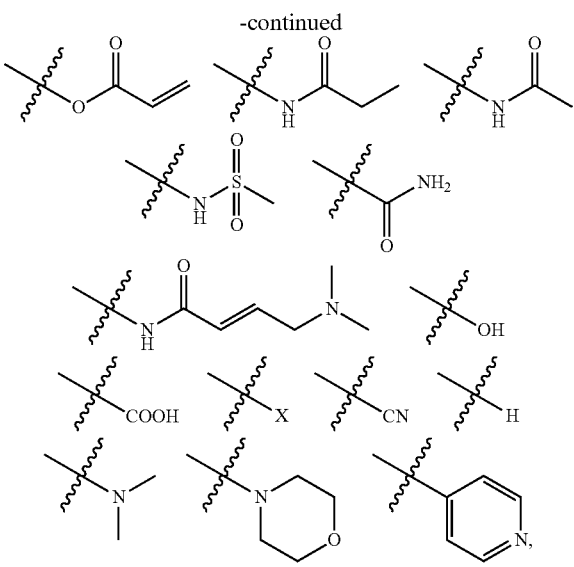

wherein, X is a halogen.

In a preferred embodiment of formula III, R³ is selected from the following groups:

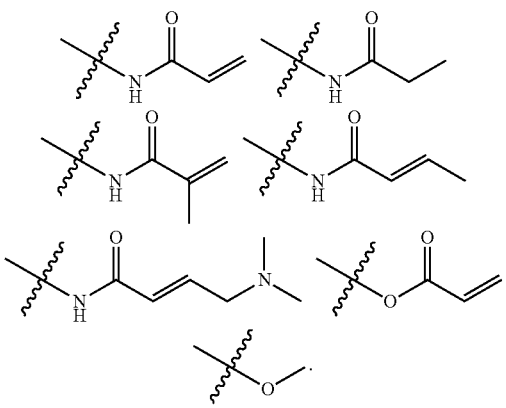

In a preferred embodiment of formula III, m is 1.

In a preferred embodiment of formula III, m is 1, and R³ is at position 4 of phenyl.

The present invention also includes the use of the compound of the present invention in the preparation of drugs for treating epidermal growth factor receptor kinase (EGFR)-mediated diseases.

The present invention also includes the use of the compound of the present invention in the preparation of drugs for treating B lymphocyte kinase (BLK) or FMS-like tyrosine kinase 3 (FLT3) mediated diseases.

In a embodiment, the disease is cancer.

In a embodiment, the cancer is selected from diffuse B-cell lymphoma, chronic lymphocytic lymphoma, chronic lymphocytic leukemia, follicular lymphoma, B-cell prolymphocytic leukemia, lymphoplasmacytic lymphoma, splenic marginal zone lymphoma, plasma cell myeloma, plasma cell tumors, extranodal marginal zone B-cell lymphoma, marginal zone of lymph nodes B-cell lymphoma, mantle cell lymphoma, thymic large B-cell lymphoma, intravascular large B-cell lymphoma, primary effusion lymphoma, Burkitt's lymphoma, lymphoma fungoides pain, lymphoblastic lymphoma, T-cell prolymphocytic leukemia, T-cell granular lymphocytic leukemia, aggressive NK-cell leukemia, cutaneous T-cell lymphoma, plastic large cell lymphoma, peripheral T-cell lymphoma, adult T-cell lymphoma, acute myelocyte leukemia, acute lymphocytic leukemia, acute promyelocytic leukemia, chronic lymphocytic leukemia, chronic myelocyte leukemia, chronic neutrophilic leukemia, acute undifferentiated leukemia, degenerative developmental large cell lymphoma, prolymphocytic leukemia, juvenile myelomonocytic leukemia, adult T-cell ALL, AML merge three lineages myelodysplasia, mixed lineage leukemia, myelodysplastic syndrome, myelodysplastic syndrome, myeloproliferative disorders, multiple myeloma.

In a embodiment, the disease is immune disease.

In a embodiment, the immune disease is selected from arthritis, lupus, inflammatory bowel disease, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, rheumatoid arthritis syndrome, multiple sclerosis, infectious neuronal inflammation, acute dissemination encephalomyelitis, Addison's disease, aplastic anemia, autoimmune hepatitis, optic neuritis, psoriasis vulgaris, graft versus host disease, transplantation, transfusion allergic reaction, allergy, I type hypersensitivity, allergic conjunctivitis, allergic rhinitis, atopic dermatitis.

In a embodiment, the cancer is selected from non-small cell lung cancer, breast cancer, prostate cancer, glial cell tumors, ovarian cancer, head and neck squamous cell carcinoma, cervical cancer, esophageal cancer, liver cancer, kidney cancer, pancreatic cancer, colon cancer, skin cancer, leukemia, lymphoma, gastric cancer, multiple myeloma, and solid tumors.

The present invention also includes the use of the compound of the present invention in the preparation of drugs for inhibiting epidermal growth factor receptor kinase (EGFR). The present invention also includes the use of the compound of the present invention in the preparation of drugs for inhibiting B lymphocyte kinase (BLK) or FMS-like tyrosine kinase 3 (FLT3).

In the present invention, the above uses of the compound of formula III are more preferred.

The present invention also includes a pharmaceutical composition comprising the compound according to the present invention, and the pharmaceutical composition may optionally comprise a pharmaceutically acceptable carrier, excipient, diluent and the like.

MODE FOR CARRYING OUT THE INVENTION

The terms mentioned herein are further defined as follows:

As used herein, "alkyl" refers to a saturated straight chain or branched chain alkyl having 1 to 10 carbon atoms, and preferably alkyl includes an alkyl with 2-8 carbon atoms, 1-6 carbon atoms, 1-4 carbon atoms, 3-8 carbon atoms, 1-3 carbon atoms in length. Examples of alkyl include, but are not limited to, methyl, ethyl, n-propyl, iso-propyl, n-butyl, iso-butyl, heptyl, and the like.

Alkyl can be substituted by one or more (e.g., 2, 3, 4, or 5) substituents, for example substituted by a halogen or a haloalkyl. For example, alkyl may be an alkyl substituted by 1-4 fluorine atoms, or an alkyl substituted by fluorinated alkyl.

As used herein, "alkoxyl" refers to an oxy substituted by alkyl. A preferred alkoxyl is an alkoxyl with 1-6 carbon atoms in length, more preferably an alkoxyl with 1-4 carbon atoms in length. Examples of alkoxyl include, but are not limited to, methoxyl, ethoxyl, propoxyl and the like.

As used herein, "alkenyl" generally means a monovalent hydrocarbon group with at least one double bond, generally comprises 2-8 carbon atoms, preferably 2-6 carbon atoms and may be straight or branched chain. Examples of alkenyl include, but are not limited to, ethenyl, propenyl, iso-propenyl, butenyl, iso-butenyl, hexenyl, and the like.

As used herein, "alkynyl" generally means a monovalent hydrocarbon group with at least one triple bond, generally comprises 2-8 carbon atoms, preferably 2-6 carbon atoms, more preferably 2-4 carbon atoms and may be straight chain or branched chain. Examples of alkenyl groups include ethynyl, propynyl, iso-propynyl, butynyl, iso-butynyl, hexynyl and the like.

As used herein, "halogen atom" or "halogen" refers to fluorine, chlorine, bromine and iodine.

"Aryl" means a monocyclic, bicyclic or tricyclic aromatic group with 6 to 14 carbon atoms, and includes phenyl, naphthyl, phenanthryl, anthryl, indenyl, fluorenyl, tetralin, indanyl and the like. Aryl can be optionally substituted with 1-5 (e.g., 1, 2, 3, 4, or 5) substituents selected from: a halogen, a $C_{1-4}$ aldehyde group, a $C_{1-6}$ alkyl, a cyano, a nitro, an amino, a hydroxyl, a hydroxymethyl, a halogen-substituted alkyl (e.g., trifluoromethyl), halogen-substituted alkoxyl (e.g., trifluoromethoxyl), a carboxyl, a $C_{1-4}$ alkoxyl, a ethoxyformyl, $N(CH_3)$ and a $C_{1-4}$ acyl, a heterocyclyl or a heteroaryl, and the like.

As used herein, "aralkyl" refers to an alkyl substituted by an aryl, for example, a $C_1$-$C_6$ alkyl substituted by a phenyl. Examples of aralkyl include, but are not limited to, arylmethyl, arylethyl, etc., such as benzyl, phenethyl and the like.

For example, aryl can be substituted by 1-3 substituents selected from: a halogen, —OH, $C_{1-4}$ alkoxyl, $C_{1-4}$ alkyl, —$NO_2$, —$NH_2$, —$N(CH_3)_2$, a carboxyl, and ethoxyformyl and the like.

As used herein, "5- or 6-member heterocycle" includes, but is not limited to, heterocyclic groups comprising 1-3 heteroatoms selected from O, S and N, including (but not limited to) a furyl, a thienyl, a pyrrolyl, a pyrrolidinyl, a pyrazolyl, an imidazolyl, a triazolyl, an oxazolyl, a pyranyl, a pyridyl, a pyrimidinyl, a pyrazinyl, a piperidinyl, a morpholinyl and the like.

As used herein, "heteroaryl" means that the group comprises 5 to 14 ring atoms, and 6, 10, or 14 electrons are shared in the ring system. And the contained ring atoms are carbon atoms and 1-3 heteroatoms optionally selected from O, N, S. Useful heteroaryl includes a piperazinyl, a morpholinyl, a piperidinyl, a pyrrolidinyl, a thienyl, a furyl, a pyranyl, a pyrrolyl, an imidazolyl, a pyrazolyl, a pyridyl, including, but not limited to, 2-pyridyl, 3-pyridyl and 4-pyridyl, a pyrazinyl, a pyrimidinyl and the like.

Heteroaryl or 5- or 6-member heterocycle may be optionally substituted by 1-5 (e.g., 1, 2, 3, 4, or 5) substituents selected from: a halogen, a $C_{1-4}$ aldehyde group, a $C_{1-6}$ a straight chain or branched chain alkyl, a cyano, a nitro, an amino, a hydroxyl, a hydroxymethyl, a halogen-substituted alkyl (e.g., trifluoromethyl), a halogen-substituted alkoxyl (e.g., trifluoromethoxyl), a carboxyl, a $C_{1-4}$ alkoxyl, a ethoxyformyl, $N(CH_3)$ and a $C_{1-4}$ acyl.

As used herein, "acyloxy" refers a group with the structure of formula "—O—C(O)—R", wherein R can be selected from an alkyl, an alkenyl and an alkynyl. And R can be optionally substituted.

As used herein, "acylamino" refers a group with the structure of formula "—R'—NH—C(O)—R", wherein, R' can be selected from a bond or an alkyl, and R can be selected from an alkyl, an alkenyl, an alkynyl, a $NR_aR_b$-substituted alkyl, a $NR_aR_b$-substituted alkenyl, a $NR_aR_b$-substituted alkynyl, a halogen-substituted alkyl, a cyano-substituted alkenyl,

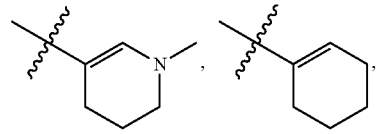

wherein $R_a$ and $R_b$ are selected from an alkyl and an alkenyl.

As used herein, "optionally substituted" means that the group modified by the term can be optionally substituted by 1-5 (e.g., 1, 2, 3, 4, or 5) substituents selected from: a halogen, a $C_{1-4}$ aldehyde group, a $C_{1-6}$ straight chain or branched chain alkyl, a cyano, a nitro, an amino, a hydroxyl, a hydroxymethyl, a halogen-substituted alkyl (e.g., trifluoromethyl), a halogen-substituted alkoxyl (e.g., trifluoromethoxyl), a carboxyl, a $C_{1-4}$ alkoxyl, an ethoxyformyl, $N(CH_3)$ and a $C_{1-4}$ acyl.

According to the present invention, a pharmaceutical composition is provided, comprising a therapeutically effective amount of the compound of formula I, II or III according to the present invention or a pharmaceutically acceptable salt thereof, and a pharmaceutically acceptable carrier or excipient.

The examples of a pharmaceutically acceptable salt of the compound according to the present invention include, but are not limited to, an inorganic and organic acid salt, such as hydrochloride, hydrobromide, sulfate, citrate, lactate, tartrate, maleate, fumarate, mandelate and oxalate; and an inorganic and organic base salt formed with a base, such as sodium hydroxyl, Tris(hydroxymethyl)aminomethane (TRIS, amine tromethamine) and N-methyl glucamine.

Each person will have different requirements, but the optimal dosage of each active ingredient in the pharmaceutical composition of the present invention can be determined by a person skilled in the art. Generally, the compound according to the present invention or a pharmaceutically acceptable salt thereof is orally administered to a mammal at dose of about 0.0025 to 50 mg/kg body weight per day; preferably, about 0.01 to 10 mg/kg body weight. For example, unit oral dose may comprise from about 0.01 to 50 mg, preferably from about 0.1 to 10 mg of compound of the invention. Unit doses may be administered for one time or more times, one or more tablets a day, with each containing from about 0.1 to 50 mg, suitably about 0.25 to 10 mg of the compound of the present invention or a solvate thereof.

The pharmaceutical composition of the present invention may be formulated into forms suitable for various routes of administration, including, but not limited to, for parenteral, subcutaneous, intravenous, intramuscular, intraperitoneal, transdermal, buccal, intrathecal, intracranial, nasal or topical routes of administration, for the treatment of cancer and other diseases. The administered amount is effective to ameliorate or eliminate one or more conditions. For the treatment of a particular disease, the effective amount is sufficient to ameliorate, or reduce the symptoms of diseases by some manner. Such doses may be administered as a single dose, or can be administered according to an effective treatment. The dose may cure the disease, but it is usually administered to improve the symptoms of the disease. Generally, repeated administration is required to achieve the desired improvement in symptoms. The dosage will be determined depending on the patient's age, health and weight, concurrent treatment, frequency of treatment, and the desired therapeutic effects.

Pharmaceutical formulations of the present invention may be administered to any mammal, as long as the therapeutic effects can be achieved. In mammals, the most important is human.

The compound or pharmaceutical composition of the present invention may be useful in the treatment or prevention of various diseases mediated by epidermal growth factor receptor kinase (EGFR). Herein, the EGFR-mediated disease is various cancers. The cancers include, but are not limited to, non-small cell lung cancer, breast cancer, prostate cancer, glial cell tumors, ovarian cancer, head and neck squamous cell carcinoma, cervical cancer, esophageal cancer, liver cancer, kidney cancer, pancreatic cancer, colon cancer, skin cancer, leukemia, lymphoma, gastric cancer, multiple myeloma, and solid tumors.

The compound or pharmaceutical composition of the present invention can be used to treat various diseases mediated by B lymphocyte kinase (BLK) or FMS-like tyrosine kinase 3 (FLT3). Herein, the diseases mediated by BLK, FLT3 are various cancers, immune diseases. The cancer includes, but not limited to, diffuse B-cell lymphoma, chronic lymphocytic lymphoma, chronic lymphocytic leukemia, follicular lymphoma, B cell prolymphocytic leukemia, lymphoplasmacytic lymphoma, splenic marginal zone lymphoma, plasma cell myeloma, plasma cell tumors, extranodal marginal zone B-cell lymphoma, marginal zone of lymph node B cell lymphoma, mantle cell lymphoma, thymic large B-cell lymphoma, intravascular large B-cell lymphoma, primary exudative lymphoma, Burkitt's lymphoma, lymphoma fungoides pain, lymphoblastic lymphoma, T cell prolymphocytic leukemia, T cell granular lymphocytic leukemia, aggressive NK-cell leukemia, cutaneous T-cell lymphoma, plastic large cell lymphoma, peripheral T-cell lymphoma, adult T-cell lymphoma, acute myelocyte leukemia, acute lymphocytic leukemia, acute promyelocytic leukemia, chronic lymphocytic leukemia, chronic myelocyte leukemia, chronic neutrophilic leukemia, acute undifferentiated leukemia, degenerative developmental large cell lymphoma, prolymphocytic leukemia, juvenile myelomonocytic leukemia, adult T cell ALL, AML merger of three lineages myelodysplasia, mixed lineage leukemia, myelodysplastic syndromes, myelodysplastic syndrome, myeloproliferative disorders, multiple myeloma. The immune diseases include, but are not limited to, arthritis, lupus, inflammatory bowel disease, rheumatoid arthritis, psoriatic arthritis, osteoarthritis, Still's disease, juvenile arthritis, diabetes, myasthenia gravis disease, Hashimoto's thyroiditis, Ord's thyroiditis, Graves' disease, rheumatoid arthritis syndrome, multiple sclerosis, infectious neuronal inflammation, acute dissemination encephalomyelitis, Addison's disease, aplastic anemia, autoimmune hepatitis, optic neuritis, psoriasis vulgaris, graft versus host disease, transplantation, transfusion allergic reaction, allergy, I type hypersensitivity, allergic conjunctivitis, allergic rhinitis, atopic dermatitis.

The pharmaceutical formulations of the present invention can be manufactured by a known method. For example, it can be manufactured by conventional mixing, granulating, dragee, dissolution, or freeze-drying process. During the manufacture of oral formulations, solid excipients and active compounds can be combined and optionally ground. If necessary, a suitable amount of auxiliary agent can be added, and the mixture of granules can be processed to obtain tablets or dragee cores.

Suitable excipients (especially fillers) are, for example, sugars such as lactose or sucrose, mannitol or sorbitol; cellulose preparations or calcium phosphates, for example tricalcium phosphate or calcium hydrogen phosphate; and binders, such as starch, including corn starch, wheat starch, rice starch, potato starch, gelatin, tragacanth, methyl cellulose, hydroxypropyl methyl cellulose, sodium carboxymethyl cellulose, or polyvinyl pyrrolidone. If desired, disintegrating agents can be added, for example, starches mentioned above as well as carboxymethyl starch, cross-linked polyvinylpyrrolidone, agar, or alginic acid or a salt thereof, such as sodium alginate. Adjuvants, especially flow modifiers and lubricants, e.g., silica, talc, stearic acid salts such as magnesium and calcium stearate, stearic acid or polyethylene glycol can be added. If necessary, suitable coatings resistant to gastric juices can be provided to the dragee core. For this purpose, concentrated sugar solutions may be applied. Such solution can contain gum arabic, talc, polyvinylpyrrolidone, polyethylene glycol and/or titanium dioxide, lacquer solutions, and suitable organic solvents or solvent mixtures. For the preparation of coatings resistant to gastric juices, an appropriate cellulose solution, for example cellulose acetate phthalate or hydroxypropylmethyl cellulose phthalate can be used. Dyestuffs or pigments may be added to the coating of tablets or dragee cores, for example, for identification or characterization of the dosage combinations of active ingredients.

Accordingly, a method for treating or preventing EGFR-mediated diseases is also provided in the present invention, comprising administering to a subject in need thereof the compound or pharmaceutical composition of the present invention.

Administration methods include, but not limited to, various administration methods known in the art, which can be determined according to the actual situation of patients. These methods include, but not limited to, parenteral, subcutaneous, intravenous, intramuscular, intraperitoneal, transdermal, buccal, intrathecal, intracranial, intranasal or topical routes.

The present invention also includes the use of the compound according to the present invention in preparing medicaments for treating EGFR, BLK or FLT3-mediated disease.

The present invention also includes the use of the compound according to the present invention in the manufacture of medicaments for inhibiting kinases, and methods of inhibiting kinases. Said method includes administering to a subject in need thereof an inhibiting effective amount or therapeutically/prophylactically effective amount of a compound or pharmaceutical composition of the present invention.

In the present invention, the subject may be a mammal, preferably a human.

In the present invention, the kinase includes, but not limited to, EGFR, BLK, FLT3, HER2, HER4, FLT1, CDK2, JAK2, LCK, LYNA, cKit, PIM1, FGFR3, FGFR1, PDGFRa, PDGFRb, KDR, SRC, ABL, AUR B, C-MET, BRAF, PKACa, IKKb, IGF1R, GSK3b, P38a and ERK1.

The present invention also includes the use of the compound according to the present invention in the manufacture of medicaments for inhibiting various diseases mediated by said kinases, and methods for treating or preventing various diseases mediated by the kinases. Said methods include administering to a subject in need thereof a therapeutically/prophylactically effective amount of the compound or pharmaceutical composition of the present invention. Said diseases mediated by kinase include, but not limited to, the previously described various cancers and immune diseases.

Synthesis of Inhibitors

The present invention will be further illustrated in the following examples. These examples are intended to illustrate the present invention, but not in any way limit the scope of the present invention.

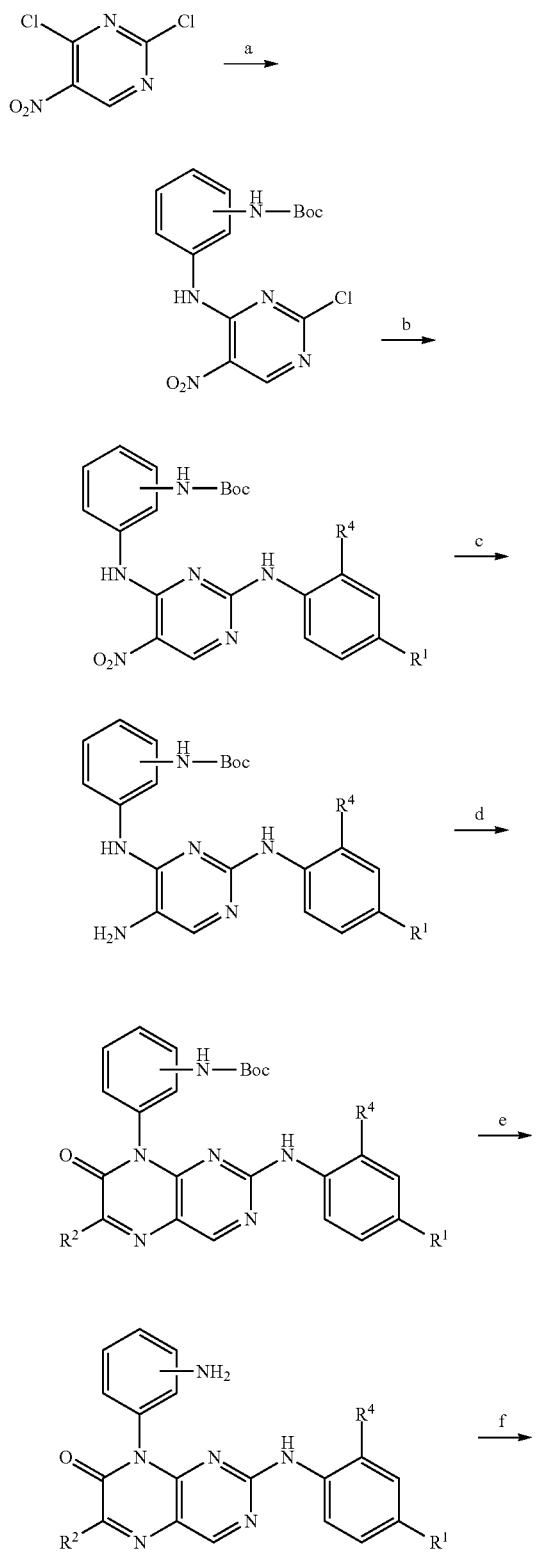

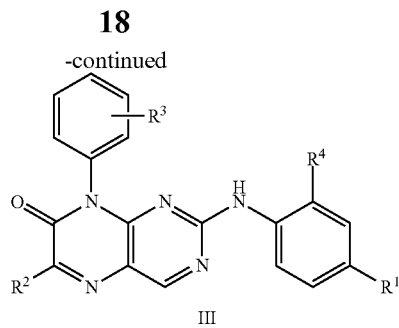

Reagents and conditions: (a) ArNH$_2$, DIPEA, 1,4-dioxane, at room temperature; (b) ArNH$_2$, DIPEA, 1,4-dioxane, at room temperature; (c) Pd/C, H$_2$, EtOH; (d) R$^2$COCOOEt, HOAc, EtOH, under reflux; (e) trifluoroacetic acid, CH$_2$Cl$_2$, 0° C. to r.t.; (f) acid chloride, Et$_3$N, CH$_2$Cl$_2$, 0° C. to r.t.; or acid chloride, 1-methyl-2-pyrrolidone, CH$_3$CN, 0° C. to r.t.

In the above preparation procedure, R$^1$-R$^4$ are defined as described above. Various starting compounds routinely obtained in the art as raw material can be used by a skilled person in the art according to actual needs to prepare the compound of the present invention.

EXAMPLE 1

The particular method for steps a-f as said above is shown as follows:

Synthesis of tert-butyl (4-(2-chloro-5-nitropyrimidyl-4-amino)phenyl)carbamate (step a)

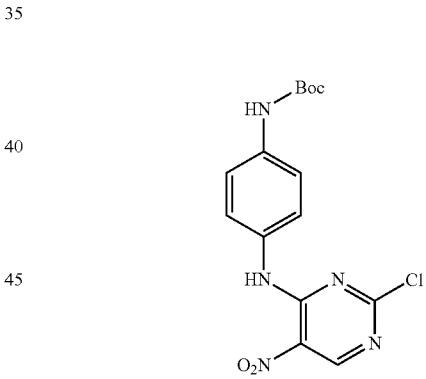

2,4-dichloro-5-nitro-pyrimidine (95 mg, 0.49 mmol) was placed into a 10 mL round bottom flask, 3 mL of 1,4-dioxane was added, and stirred at room temperature. Tert-butyl (4-aminophenyl) carbamate (100 mg, 0.48 mmol) and N,N-diisopropylethylamine (69 mg, 0.53 mmol) were dissolved in 2 mL of 1,4-dioxane. The resulting solution was added dropwise into the reaction solution as said above. Upon completion of addition, the resulting mixture was stirred at room temperature for 0.5 h, and TLC showed that the raw material was completely conversed. The solvent was removed by rotary evaporation, and the crude product was separated through silica gel column chromatography (petroleum ether/ethyl acetate=10:1, V/V) to obtain tert-butyl (4-(2-chloro-5-nitropyrimidyl-4-amino)-phenyl)carbamate as orange solids (144 mg, yield 82%). $^1$H NMR (400 MHz, DMSO-d$_6$): δ 10.38 (s, 1H), 9.46 (s, 1H), 9.12 (s, 1H), 7.49 (d, J=8.6 Hz, 2H), 7.39 (d, J=8.6 Hz, 2H), 1.49 (s, 9H).

Synthesis of tert-butyl (4-(2-(4-methoxyphenylamino)-5-nitro-pyrimidyl-4-amino)phenyl) carbamate (step b)

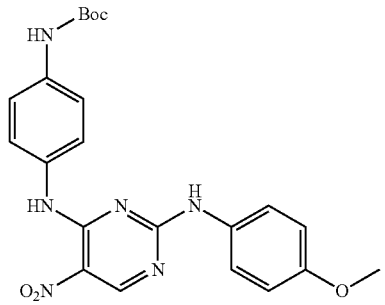 [SMILES: COc1ccc(Nc2ncc([N+](=O)[O-])c(Nc3ccc(NC(=O)OC(C)(C)C)cc3)n2)cc1]

Tert-butyl (4-(2-chloro-5-nitropyrimidyl-4-amino)phenyl) carbamate (50 mg, 0.14 mmol), p-anisidine (17 mg, 0.14 mmol), N,N-diisopropylethylamine (18 mg, 0.18 mmol) were placed into a 10 mL round bottom flask, 5 mL of 1,4-dioxane was added, and stirred at room temperature for 4 hours. TLC showed that the raw material was completely conversed. The solvent was removed by rotary evaporation, and the crude product was purified through silica gel column chromatography (petroleum ether/ethyl acetate=4:1, V/V) to obtain tert-butyl (4-(2-(4-methoxyphenylamino)-5-nitro-pyrimidyl-4-amino)phenyl) carbamate as yellow solids (51 mg, yield 82%). $^1$H NMR (400 MHz, DMSO-$d_6$): δ 10.30 (s, 1H), 10.26 (s, 1H), 9.45 (s, 1H), 9.04 (s, 1H), 7.49 (d, J=8.8 Hz, 2H), 7.45 (d, J=8.8 Hz, 2H), 7.40 (d, J=8.6 Hz, 2H), 6.75 (d, J=8.6 Hz, 2H), 3.73 (s, 3H), 1.50 (s, 9H).

Synthesis of tert-butyl (4-(5-amino-2-(4-methoxyphenylamino)pyrimidyl-4-amino)phenyl) carbamate (Step c)

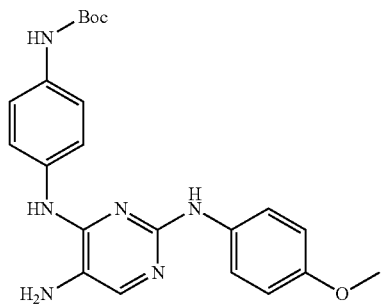 [SMILES: COc1ccc(Nc2ncc(N)c(Nc3ccc(NC(=O)OC(C)(C)C)cc3)n2)cc1]

Tert-butyl (4-(2-(4-methoxy-phenylamino)-5-nitro-pyrimidyl-4-amino)phenyl) carbamate (45 mg, 0.10 mmol) was placed into a 50 mL round bottom flask. 20 mL of ethanol, and 5 mg of palladium on carbon (10% Pd) were added, hydrogen was filled, and the resulting reaction system was stirred at room temperature overnight. Upon the completion of reaction, the system was filtered, and the filtrate was spin-dried. The crude product was purified through silica gel column chromatography (dichloromethane/methanol=5:1, V/V) to give tert-butyl (4-(5-amino-2-(4-methoxylphenylamino)-pyrimidyl-4-amino)phenyl) carbamate as pale pink solids (30 mg, yield 83%). $^1$H NMR (400 MHz, DMSO-$d_6$): δ 9.23 (s, 1H), 8.42 (s, 1H), 8.10 (s, 1H), 7.62 (d, J=9.2 Hz, 2H), 7.56 (s, 1H), 7.53 (d, J=9.2 Hz, 2H), 7.40 (d, J=8.8 Hz, 2H), 6.77 (d, J=8.8 Hz, 2H), 3.70 (s, 3H), 1.48 (s, 9H).

Synthesis of tert-butyl (4-(2-(4-methoxyphenylamino)-7-oxo-8(7H)-pteridin-yl)-phenyl) carbamate (step d)

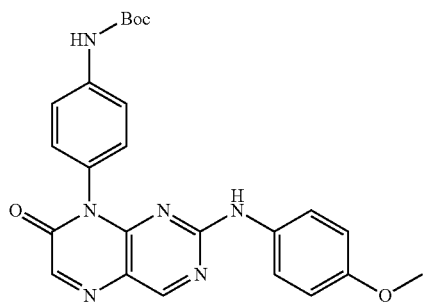 [SMILES: COc1ccc(Nc2ncc3ncc(=O)n(-c4ccc(NC(=O)OC(C)(C)C)cc4)c3n2)cc1]

Tert-butyl (4-(5-amino-2-(4-methoxyphenylamino)pyrimidinyl-4-amino)phenyl) carbamate (30 mg, 0.07 mmol) was added into a 10 mL round bottom flask. 0.29 mL of glacial acetic acid and 5 mL of anhydrous ethanol were added, and then ethyl glyoxylate (50% in toluene) (16 mg, 0.08 mmol) was added. The resulting reaction mixture was heated to reflux and stirred overnight. Upon completion, solids precipitated. The solids were filtered, and the filter cake was washed with ethanol, ammonia water and deionized water, and dried, to give tert-butyl (4-(2-(4-methoxyphenylamino)-7-oxo-8(7H)-pteridin-yl)phenyl) carbamate as yellow solids (18 mg, yield 76%). $^1$H NMR (400 MHz, DMSO-$d_6$): δ 10.08 (s, 1H), 9.64 (s, 1H), 8.84 (s, 1H), 8.03 (s, 1H), 7.65 (d, J=8.4 Hz, 2H), 7.30-7.28 (m, 4H), 6.61 (br, 2H), 3.67 (s, 3H), 1.52 (s, 9H).

Synthesis of 8-(4-aminophenyl)-2-(4-methoxyphenyl)-7(8H)-pteridin-one (Compound 001) (step e)

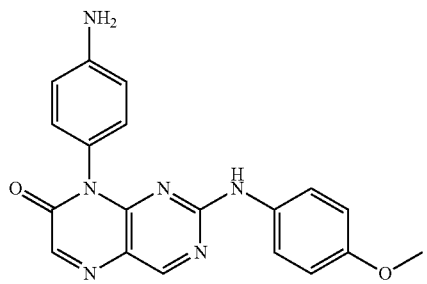 [SMILES: COc1ccc(Nc2ncc3ncc(=O)n(-c4ccc(N)cc4)c3n2)cc1]

Tert-butyl (4-(2-(4-methoxyphenylamino)-7-oxo-8(7H)-pteridin-yl)phenyl) carbamate (18 mg, 0.04 mmol) was placed a 5 mL round bottom flask. 2 mL of dichloromethane was added, and the resulting mixture was stirred at 0° C. 0.5 mL of trifluoroacetic acid was added, and the resulting mixture was stirred at 0° C. for 1 hour, and then at room temperature for another 1 hour. After the reaction was completed, a saturated sodium bicarbonate solution was added to neutralize the solution to alkaline, and the resulting mixture was extracted with dichloromethane (3×50 mL).

The organic phase was washed with deionized water, and a saturated sodium chloride solution, and dried over anhydrous sodium sulfate. The solvent was spin-dried to obtained 8-(4-aminophenyl)-2-(4-methoxyphenyl)-7(8H)-pteridin-one as yellow solids (14 mg, yield 99%). $^1$H NMR (400 MHz, DMSO-d$_6$): δ 10.04 (br, 1H), 8.81 (s, 1H), 8.00 (s, 1H), 7.40 (d, J=7.6 Hz, 2H), 6.98 (d, J=8.4 Hz, 2H), 6.73 (d, J=8.4 Hz, 2H), 6.67 (br, 2H), 5.44 (s, 2H), 3.70 (s, 3H). $^{13}$C NMR (100 MHz, DMSO-d$_6$): δ 159.19, 158.53, 157.17, 154.95, 151.76, 149.66, 146.68, 133.17, 129.22, 122.66, 121.04, 120.70, 114.37, 113.87, 55.55. HRMS (ESI) calculated for C$_{19}$H$_{17}$N$_6$O$_2$ [M+H]$^+$ 361.1413. found 361.1414.

Synthesis of N-(4-(2-(4-methoxyphenylamino)-7-oxo-8(7H)-pteridin-yl)phenyl)acrylamide (Compound 002) (step f)

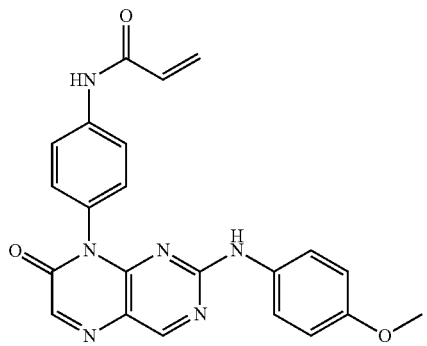 [SMILES: C=CC(=O)Nc1ccc(-n2c(=O)cnc3cnc(Nc4ccc(OC)cc4)nc32)cc1]

8-(4-aminophenyl)-2-(4-methoxyphenyl)-7(8H)-pteridin-one (100 mg, 0.28 mmol) was placed in a 100 mL round bottom flask. 50 mL of dichloromethane, and triethylamine (28 mg, 0.28 mmol) were added, and the resulting mixture was stirred at 0° C. Acryloyl chloride (29 mg, 0.31 mmol) was dissolved in 5 mL of dichloromethane and added dropwise to the above reaction solution. Upon addition, the resulting reaction mixture was stirred at room temperature overnight. The solvent was removed by rotary evaporation, and the crude product was purified by silica gel column chromatography (dichloromethane/ethyl acetate=5:1, v/v) to obtain N-(4-(2-(4-methoxyphenylamino)-7-oxo-8(7H)-pteridin-yl)phenyl) acrylamide as yellow solids (34 mg, yield 30%). $^1$H NMR (400 MHz, DMSO-d$_6$): δ 10.42 (s, 1H), 10.07 (br, 1H), 8.84 (s, 1H), 8.04 (s, 1H), 7.87 (d, J=8.8 Hz, 2H), 7.38 (d, J=8.8 Hz, 2H), 7.30 (br, 2H), 6.59 (br, 2H), 6.52 (dd, J=17.0, 10.0 Hz, 1H), 6.33 (dd, J=17.0, 1.8 Hz, 1H), 5.82 (dd, J=10.0, 1.8 Hz, 1H), 3.62 (s, 3H). $^{13}$C NMR (100 MHz, DMSO-d$_6$): δ 163.90, 159.28, 158.51, 156.68, 155.02, 151.44, 146.65, 139.72, 133.00, 130.18, 129.50, 127.72, 121.02, 120.61, 113.77, 55.40. HRMS (ESI) calculated for C$_{22}$H$_{19}$N$_6$O$_3$ [M+H]$^+$ 415.1519. found 415.1515.

The following compounds were synthesized according to the above steps a-f:

N-(4-(2-(4-morpholino-phenylamino)-7-oxo-8(7H)-pteridin-yl)phenyl)acrylamide (Compound 003)

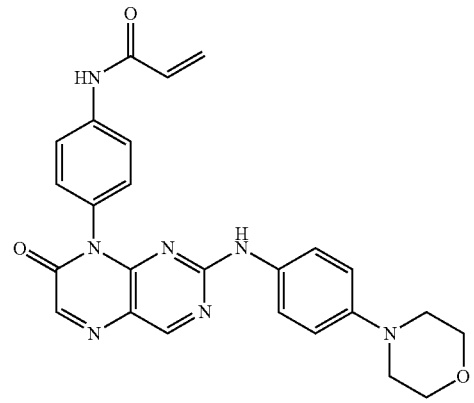 [SMILES: C=CC(=O)Nc1ccc(-n2c(=O)cnc3cnc(Nc4ccc(N5CCOCC5)cc4)nc32)cc1]

$^1$H NMR (400 MHz, DMSO-d$_6$): δ 10.44 (s, 1H), 10.00 (s, 1H), 8.82 (s, 1H), 8.02 (s, 1H), 7.88 (d, J=8.0 Hz, 1H), 7.36 (d, J=8.4 Hz, 1H), 7.22 (br, 2H), 6.59 (br, 2H), 6.52 (dd, J=17.2, 10.2 Hz, 1H), 6.33 (d, J=17.2 Hz, 1H), 5.85 (d, J=10.2 Hz, 1H), 3.67 (br, 4H), 2.92 (br, 4H). HRMS (ESI) calculated for C$_{25}$H$_{24}$N$_7$O$_3$ [M+H]$^+$ 470.1941. found 470.1932.

N-(4-(2-(4-methoxyphenylamino)-6-methyl-7-oxo-8(7H)-pteridin-yl)phenyl)acrylamide (Compound 004)

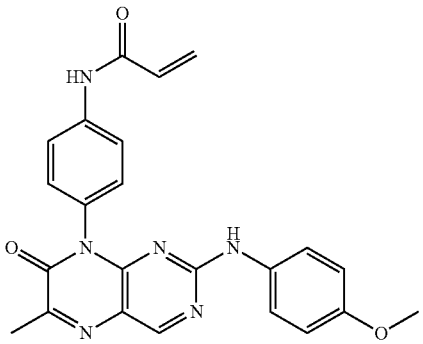 [SMILES: C=CC(=O)Nc1ccc(-n2c(=O)c(C)nc3cnc(Nc4ccc(OC)cc4)nc32)cc1]

$^1$H NMR (400 MHz, DMSO-d$_6$): δ 10.44 (s, 1H), 9.90 (br, 1H), 8.77 (s, 1H), 7.87 (d, J=8.8 Hz, 2H), 7.50 (d, J=8.8 Hz, 2H), 7.29 (br, 2H), 6.59 (br, 2H), 6.52 (dd, J=17.0, 10.0 Hz, 1H), 6.33 (dd, J=17.0, 1.9 Hz, 1H), 5.82 (dd, J=10.0, 1.9 Hz, 1H), 3.61 (s, 3H), 2.42 (s, 3H). HRMS (ESI) calculated for C$_{23}$H$_{21}$N$_6$O$_3$ [M+H]$^+$ 429.1675. found 429.1671.

8-(3-aminophenyl)-2-(4-methoxyphenyl)-7(8H)-pteridin-one (Compound 005)

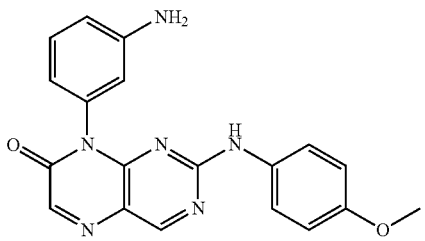 [SMILES: COc1ccc(Nc2ncc3ncc(=O)n(-c4cccc(N)c4)c3n2)cc1]

¹H NMR (400 MHz, DMSO-d₆): δ 10.06 (br, 1H), 8.83 (s, 1H), 8.01 (s, 1H), 7.41 (d, J=8.0 Hz, 2H), 7.22 (t, J=8.0 Hz, 1H), 6.75 (d, J=7.6 Hz, 1H), 6.67 (br, 2H), 6.53 (s, 1H), 6.48 (d, J=7.6 Hz, 1H), 5.35 (s, 2H), 3.69 (s, 3H). HRMS (ESI) calculated for $C_{19}H_{17}N_6O_2$ [M+H]⁺ 361.1413. found 361.1413.

N-(3-(2-(4-methoxyphenylamino)-7-oxo-8(7H)-pteridin-yl)phenyl) acrylamide (Compound 006)

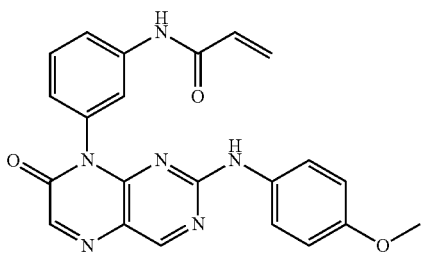 [SMILES: C=CC(=O)Nc1cccc(-n2c(=O)cnc3cnc(Nc4ccc(OC)cc4)nc32)c1]

¹H NMR (400 MHz, DMSO-d₆): δ 10.42 (s, 1H), 10.10 (br, 1H), 8.85 (s, 1H), 8.05 (s, 1H), 7.84 (d, J=8.0 Hz, 1H), 7.78 (s, 1H), 7.56 (t, J=8.0 Hz, 1H), 7.31 (br, 2H), 7.13 (d, J=8.0 Hz, 1H), 6.58 (br, 2H), 6.45 (dd, J=16.8, 10.4 Hz, 1H), 6.26 (dd, J=16.8, 1.6 Hz, 1H), 5.77 (dd, J=10.4, 1.6 Hz, 1H), 3.65 (s, 3H). HRMS (ESI) calculated for $C_{22}H_{19}N_6O_3$ [M+H]⁺ 415.1519. found 415.1516.

N-(3-(2-(4-methoxyphenylamino)-7-oxo-8(7H)-pteridin-yl)phenyl) propionamide (Compound 007)

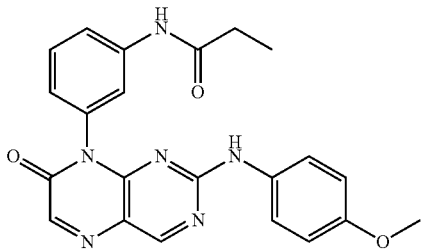 [SMILES: CCC(=O)Nc1cccc(-n2c(=O)cnc3cnc(Nc4ccc(OC)cc4)nc32)c1]

¹H NMR (400 MHz, DMSO-d₆): δ 10.13 (s, 1H), 10.09 (s, 1H), 8.85 (s, 1H), 8.04 (s, 1H), 7.74 (d, J=8.0 Hz, 1H), 7.71 (s, 1H), 7.53 (t, J=8.0 Hz, 1H), 7.31 (br, 2H), 7.07 (d, J=8.0 Hz, 1H), 6.59 (br, 2H), 3.67 (s, 3H), 2.33 (q, J=7.6 Hz, 2H), 1.07 (t, J=7.6 Hz, 3H). HRMS (ESI) calculated for $C_{22}H_{21}N_6O_3$ [M+H]⁺ 417.1675. found 417.1678.

N-(4-(2-(4-methoxyphenylamino)-7-oxo-8(7H)-pteridin-yl)phenyl) propionamide (Compound 008)

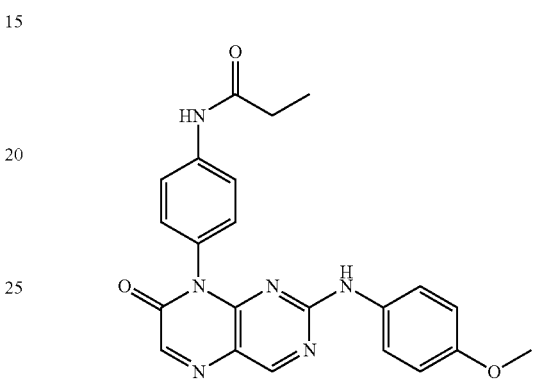

¹H NMR (400 MHz, DMSO-d₆): δ 10.15 (s, 1H), 10.08 (br, 1H), 8.85 (s, 1H), 8.04 (s, 1H), 7.80 (d, J=8.4 Hz, 2H), 7.35-7.33 (m, 4H), 6.61 (br, 2H), 3.67 (s, 3H), 2.41 (q, J=7.6 Hz, 2H), 1.14 (t, J=7.6 Hz, 3H). HRMS (ESI) calculated for $C_{22}H_{21}N_6O_3$ [M+H]⁺ 417.1675. found 417.1674.

4-(dimethylamino)-N-(4-(2-(4-methoxyphenylamino)-7-oxo-8(7H)-pteridin-yl)phenyl)-2-buteneamide (Compound 009)

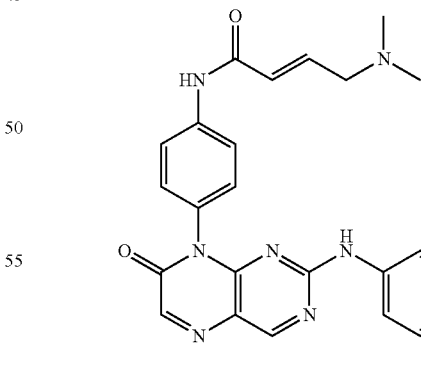

¹H NMR (400 MHz, DMSO-d₆): δ 10.45 (s, 1H), 10.10 (br, 1H), 8.85 (s, 1H), 8.05 (s, 1H), 7.87 (d, J=8.8 Hz, 2H), 7.37 (d, J=8.8 Hz, 2H), 7.30 (br, 2H), 6.82 (td, J=15.4, 6.0 Hz, 1H), 6.60 (br, 2H), 6.40 (d, J=15.4 Hz, 1H), 3.63 (s, 3H), 3.27 (d, J=5.2 Hz, 2H), 2.33 (s, 6H). HRMS (ESI) calculated for $C_{25}H_{26}N_7O_3$ [M+H]⁺ 472.2097. found 472.2095.

4-(dimethylamino)-N-(3-(2-(4-methoxyphenylamino)-7-oxo-8(7H)-pteridin-yl)phenyl)-2-buteneamide (Compound 010)

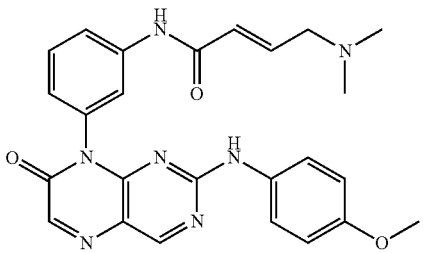 [SMILES: COc1ccc(Nc2ncc3ncc(=O)n(-c4cccc(NC(=O)/C=C/CN(C)C)c4)c3n2)cc1]

¹H NMR (400 MHz, DMSO-d₆): δ 10.33 (s, 1H), 10.08 (br, 1H), 8.86 (s, 1H), 8.05 (s, 1H), 7.83 (d, J=8.0 Hz, 1H), 7.78 (s, 1H), 7.55 (t, J=8.0 Hz, 1H), 7.32 (br, 2H), 7.11 (d, J=8.0 Hz, 1H), 6.74 (td, J=15.2, 5.6 Hz, 1H), 6.59 (br, 2H) 6.30 (d, J=15.2 Hz, 1H), 3.66 (s, 3H), 3.06 (d, J=5.6 Hz, 2H), 2.17 (s, 6H). HRMS (ESI) calculated for $C_{25}H_{24}N_7O_3$ [M+H]⁺ 472.2097. found 472.2094.

4-(2 (4-methoxyphenylamino)-7-oxo-8(7H)-pteridin-yl)phenyl acrylate (Compound 011)

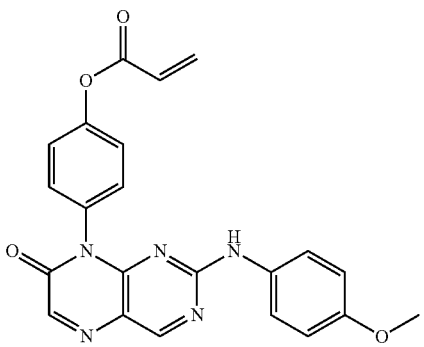 [SMILES: C=CC(=O)Oc1ccc(-n2c(=O)cnc3cnc(Nc4ccc(OC)cc4)nc32)cc1]

¹H NMR (400 MHz, DMSO-d₆): δ 10.15 (s, 1H), 8.87 (s, 1H), 8.06 (s, 1H), 7.51 (d, J=8.8 Hz, 2H), 7.45 (d, J=8.8 Hz, 2H), 7.31 (br, 2H), 6.69 (br, 2H), 6.60 (dd, J=17.2, 1.6 Hz, 1H), 6.51 (dd, J=17.2, 9.9 Hz, 1H), 6.22 (dd, J=9.9, 1.6 Hz, 1H), 3.67 (s, 3H). HRMS (ESI) calculated for $C_{22}H_{18}N_5O_4$ [M+H]⁺ 416.1359. found 416.1359.

4-(dimethylamino)-N-(4-(7-oxo-2-(phenylamino)-8 (7H)-pteridin-yl)phenyl)-2-buteneamide (Compound 012)

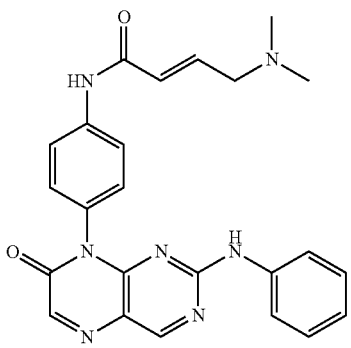 [SMILES: CN(C)C/C=C/C(=O)Nc1ccc(-n2c(=O)cnc3cnc(Nc4ccccc4)nc32)cc1]

¹H NMR (400 MHz, DMSO-d₆): δ 10.37 (s, 1H), 10.19 (br, 1H), 8.90 (s, 1H), 8.08 (s, 1H), 7.87 (d, J=8.4 Hz, 2H), 7.42 (d, J=7.6 Hz, 2H), 7.38 (d, J=8.4 Hz, 2H), 7.03 (br, 1H), 6.88 (t, J=7.6 Hz, 1H), 6.82 (td, J=15.4, 5.6 Hz, 1H), 6.37 (d, J=15.4 Hz, 1H), 3.14 (d, J=5.6 Hz, 2H), 2.24 (s, 6H). HRMS (ESI) calculated for $C_{24}H_{24}N_7O_2$ [M+H]⁺ 442.1991. found 442.1989.

4-(dimethylamino)-N-(3-(7-oxo-2-(phenylamino)-8 (7H)-pteridin-yl)phenyl)-2-buteneamide (Compound 013)

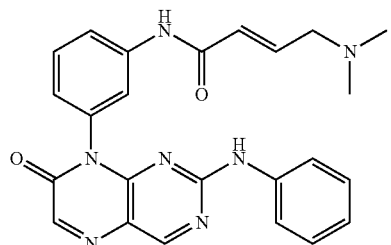

¹H NMR (400 MHz, DMSO-d₆): δ 10.32 (s, 1H), 10.17 (s, 1H), 8.90 (s, 1H), 8.08 (s, 1H), 7.81-7.79 (m, 2H), 7.55 (t, J=8.0 Hz, 1H), 7.41 (d, J=7.2 Hz, 2H), 7.12 (d, J=8.0 Hz, 1H), 7.01 (br, 2H), 6.87 (t, J=7.2 Hz, 1H), 6.73 (td, J=15.2, 5.6 Hz, 1H), 6.28 (d, J=15.2 Hz, 1H), 3.05 (d, J=5.6 Hz, 2H), 2.16 (s, 6H). HRMS (ESI) calculated for $C_{24}H_{24}N_7O_2$ [M+H]⁺ 442.1991. found 442.1996

N-(4-(7-oxo-2-(phenylamino)-8(7H)-pteridin-yl) phenyl) acrylamide (Compound 014)

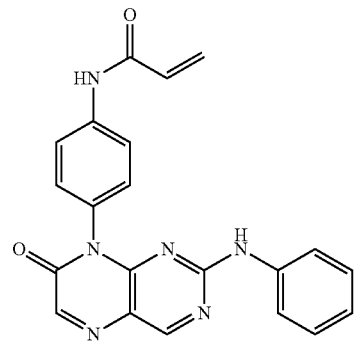 [SMILES: C=CC(=O)Nc1ccc(-n2c(=O)cnc3cnc(Nc4ccccc4)nc32)cc1]

¹H NMR (400 MHz, DMSO-d₆): δ 10.44 (s, 1H), 10.19 (br, 1H), 8.90 (s, 1H), 8.09 (s, 1H), 7.88 (d, J=8.4 Hz, 2H), 7.41-7.38 (m, 4H), 7.03 (br, 2H), 6.88 (t, J=7.2 Hz, 1H), 6.53 (dd, J=16.8, 10.4 Hz, 1H), 6.35 (dd, J=16.8, 1.6 Hz, 1H), 5.84 (dd, J=10.4, 1.6 Hz, 1H). HRMS (ESI) calculated for $C_{21}H_{17}N_6O_2$ [M+H]⁺ 385.1413. found 385.1405.

N-(3-(7-oxo-2-(phenylamino)-8(7H)-pteridin-yl) phenyl)acrylamide (Compound 015)

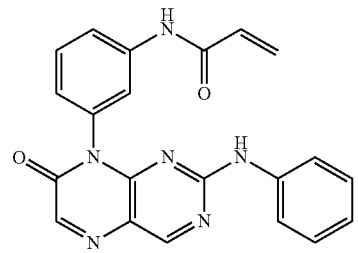 [SMILES: C=CC(=O)Nc1cccc(-n2c(=O)cnc3cnc(Nc4ccccc4)nc32)c1]

¹H NMR (400 MHz, DMSO-d₆): δ 10.42 (s, 1H), 10.19 (s, 1H), 8.91 (s, 1H), 8.09 (s, 1H), 7.84-7.81 (m, 2H), 7.57

(t, J=8.0 Hz, 1H), 7.41 (br, 2H), 7.15 (d, J=7.6 Hz, 1H), 7.02 (br, 2H), 6.87 (t, J=7.6 Hz, 1H), 6.45 (dd, J=16.8, 10.4 Hz, 1H), 6.26 (dd, J=16.8, 1.6 Hz, 1H), 5.77 (dd, J=10.4, 1.6 Hz, 1H). HRMS (ESI) calculated for $C_{21}H_{17}N_6O_2$ [M+H]$^+$ 385.1413. found 385.1413.

N-(4-(2-(4-chlorophenylamino)-7-oxo-8(7H)-pteridin-yl)phenyl) acrylamide (Compound 016)

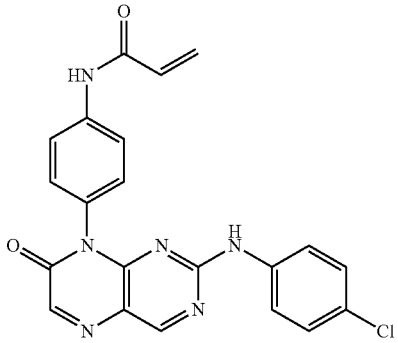 [SMILES: C=CC(=O)Nc1ccc(-n2c(=O)cnc3cnc(Nc4ccc(Cl)cc4)nc32)cc1]

$^1$H NMR (400 MHz, DMSO-d$_6$): δ 10.46 (s, 1H), 10.34 (s, 1H), 8.92 (s, 1H), 8.11 (s, 1H), 7.88 (d, J=8.8 Hz, 2H), 7.41-7.36 (m, 4H), 7.06 (br, 2H), 6.53 (dd, J=16.8, 10.4 Hz, 1H), 6.36 (dd, J=16.8, 1.6 Hz, 1H), 5.84 (dd, J=10.4, 1.6 Hz, 1H). HRMS (ESI) calculated for $C_{21}H_{16}N_6O_2Cl$ [M+H]$^+$ 419.1023. found 419.1031.

N-(3-(2-(4-chlorophenylamino)-7-oxo-8(7H)-pteridin-yl)phenyl) acrylamide (Compound 017)

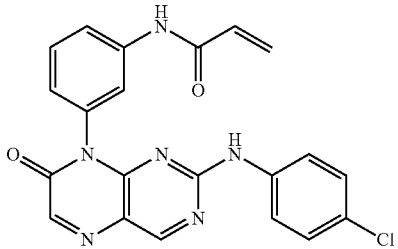 [SMILES: C=CC(=O)Nc1cccc(-n2c(=O)cnc3cnc(Nc4ccc(Cl)cc4)nc32)c1]

$^1$H NMR (400 MHz, DMSO-d$_6$): δ 10.44 (s, 1H), 10.34 (br, 1H), 8.93 (s, 1H), 8.11 (s, 1H), 7.84 (s, 1H), 7.81 (d, J=8.4 Hz, 1H), 7.59 (t, J=8.0 Hz, 1H), 7.43 (d, J=7.2 Hz, 2H), 7.15 (d, J=7.6 Hz, 1H), 6.46 (dd, J=16.8, 10.4 Hz, 1H), 6.26 (dd, J=16.8, 1.8 Hz, 1H), 5.77 (dd, J=10.12, 1.8 Hz, 1H). HRMS (ESI) calculated for $C_{21}H_{16}N_6O_2Cl$ [M+H]$^+$ 419.1023. found 419.1027.

N-(3-(2-(4-morpholinophenylamino)-7-oxo-8(7H)-pteridin-yl)phenyl) acrylamide (Compound 018)

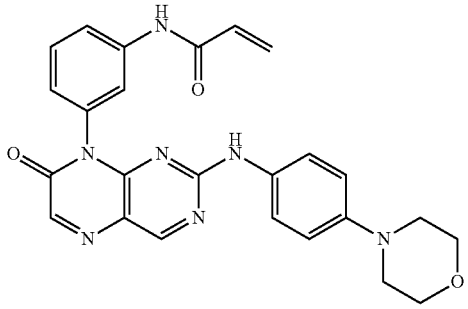 [SMILES: C=CC(=O)Nc1cccc(-n2c(=O)cnc3cnc(Nc4ccc(N5CCOCC5)cc4)nc32)c1]

$^1$H NMR (400 MHz, DMSO-d$_6$): δ 10.43 (s, 1H), 10.06 (s, 1H), 8.84 (s, 1H), 8.03 (s, 1H), 7.92 (br, 1H), 7.72 (s, 1H), 7.56 (t, J=7.6 Hz, 1H), 7.27 (br, 2H), 7.12 (d, J=7.2 Hz, 1H), 6.58 (br, 2H), 6.45 (dd, J=16.8, 10.4 Hz, 1H), 6.26 (d, J=16.8 Hz, 1H), 5.78 (d, J=10.4 Hz, 1H), 3.71 (br, 4H), 2.94 (br, 4H). HRMS (ESI) calculated for $C_{25}H_{24}N_7O_3$ [M+H]$^+$ 470.1941. found 470.1939.

N-(4-(2-(4-(4-methyl-1-piperazinyl)-phenylamino)-7-oxo-8(7H)-pteridin-yl)phenyl) acrylamide (Compound 019)

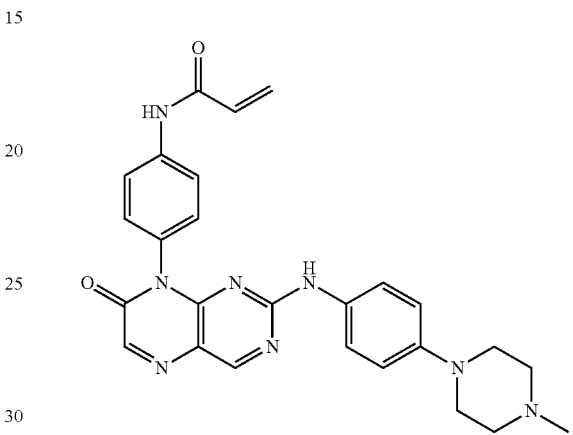

$^1$H NMR (400 MHz, DMSO-d$_6$): δ 10.51 (s, 1H), 10.06 (s, 1H), 8.83 (s, 1H), 8.03 (s, 1H), 7.89 (d, J=8.4 Hz, 2H), 7.37 (d, J=8.4 Hz, 2H), 7.17 (d, J=6.4 Hz, 1H), 6.56-6.49 (m, 3H), 6.34 (d, J=16.8 Hz, 1H), 5.85 (d, J=10.8 Hz, 1H), 2.94 (br, 4H), 2.37 (br, 4H), 2.20 (s, 3H). HRMS (ESI) calculated for $C_{26}H_{27}N_8O_2$ [M+H]$^+$ 483.2257. found 483.2259.

N-(3-(2-(4-(4-methyl-1-piperazinyl)-phenylamino)-7-oxo-8(7H)-pteridin-yl)phenyl) acrylamide (Compound 020)

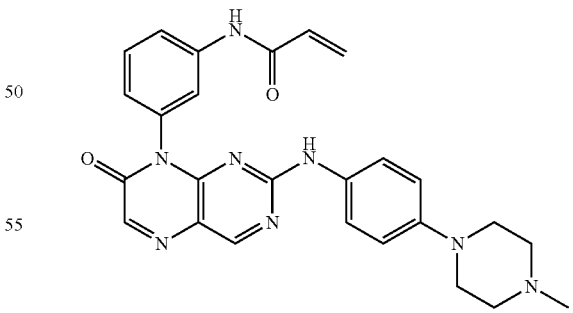

$^1$H NMR (400 MHz, DMSO-d$_6$): δ 10.45 (s, 1H), 10.06 (s, 1H), 8.84 (s, 1H), 8.04 (s, 1H), 7.93 (br, 1H), 7.73 (s, 1H), 7.56 (t, J=8.0 Hz, 1H), 7.25 (br, 2H), 7.12 (d, J=8.0 Hz, 1H), 6.57 (br, 2H), 6.46 (dd, J=16.8, 10.4 Hz, 1H), 6.27 (dd, J=16.8, 1.8 Hz, 1H), 5.78 (dd, J=10.4, 1.8 Hz, 1H), 2.98 (br, 4H), 2.42 (br, 4H), 2.22 (s, 3H). HRMS (ESI) calculated for $C_{26}H_{27}N_8O_2$ [M+H]$^+$ 483.2257. found 483.2259.

N-(3-(7-oxo-2-(4-(1-piperidinyl)phenylamino)-8 (7H)-pteridinyl)phenyl) acrylamide (Compound 021)

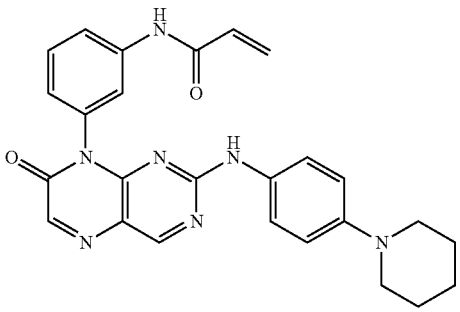 [SMILES: C=CC(=O)Nc1cccc(-n2c(=O)cnc3cnc(Nc4ccc(N5CCCCC5)cc4)nc32)c1]

¹H NMR (400 MHz, DMSO-d₆): δ 10.44 (s, 1H), 10.03 (s, 1H), 8.83 (s, 1H), 8.02 (s, 1H), 7.94 (br, 1H), 7.73 (s, 1H), 7.55 (t, J=8.0 Hz, 1H), 7.24 (br, 2H), 7.11 (d, J=8.0 Hz, 1H), 6.57 (br, 2H), 6.46 (dd, J=17.0, 10.2 Hz, 1H), 6.26 (dd, J=17.0, 1.8 Hz, 1H), 5.77 (dd, J=10.2, 1.8 Hz, 1H), 2.95 (br, 4H), 1.57 (br, 4H), 1.49 (br, 2H). HRMS (ESI) calculated for $C_{26}H_{26}N_7O_2$ [M+H]⁺ 468.2148. found 468.2146.

N-(3-(7-oxo-2-(4-(1-pyrrolidinyl)phenylamino)-8 (7H)-pteridin-yl)phenyl) acrylamide (Compound 022)

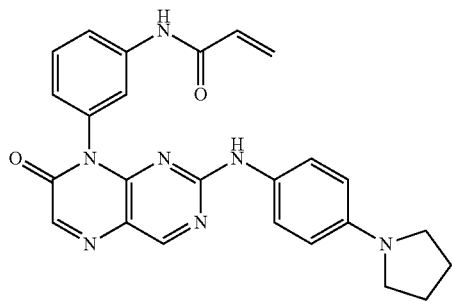 [SMILES: C=CC(=O)Nc1cccc(-n2c(=O)cnc3cnc(Nc4ccc(N5CCCC5)cc4)nc32)c1]

¹H NMR (400 MHz, DMSO-d₆): δ 10.40 (s, 1H), 9.92 (s, 1H), 8.79 (s, 1H), 7.99 (s, 1H), 7.90 (br, 1H), 7.74 (br, 1H), 7.54 (t, J=8.0 Hz, 1H), 7.20 (br, 2H), 7.10 (d, J=8.0 Hz, 1H), 6.46 (dd, J=17.0, 10.2 Hz, 1H), 6.26 (dd, J=17.0, 1.8 Hz, 1H), 6.20 (br, 2H), 5.77 (dd, J=10.2, 1.8 Hz, 1H), 3.10 (br, 4H), 1.91 (br, 4H). HRMS (ESI) calculated for $C_{25}H_{24}N_7O_2$ [M+H]⁺ 454.1991. found 454.1995.

N-(3-(2-(4-(diethylamino)phenylamino)-7-oxo-8 (7H)-pteridin-yl)phenyl) acrylamide (Compound 023)

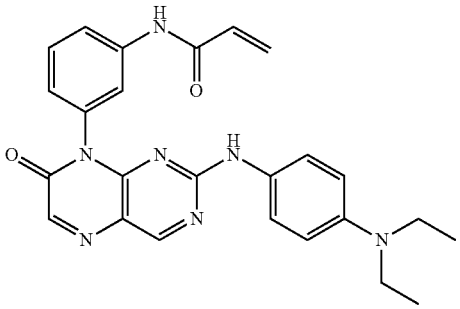 [SMILES: C=CC(=O)Nc1cccc(-n2c(=O)cnc3cnc(Nc4ccc(N(CC)CC)cc4)nc32)c1]

¹H NMR (400 MHz, DMSO-d₆): δ 10.42 (s, 1H), 9.92 (s, 1H), 8.80 (s, 1H), 8.00 (s, 1H), 7.92 (br, 1H), 7.73 (s, 1H), 7.53 (t, J=8.0 Hz, 1H), 7.19 (br, 2H), 7.09 (d, J=8.0 Hz, 1H), 6.46 (dd, J=17.0, 10.2 Hz, 1H), 6.32 (br, 2H), 6.27 (dd, J=17.0, 1.8 Hz, 1H), 5.76 (dd, J=10.2, 1.8 Hz, 1H), 3.20 (br, 4H), 1.00 (t, J=6.8 Hz, 6H). HRMS (ESI) calculated for $C_{25}H_{26}N_7O_2$ [M+H]⁺ 456.2148. found 456.2143.

N-(3-(2-(4-(acetylamino)-phenylamino)-7-oxo-8 (7H)-pteridin-yl)phenyl) acrylamide (Compound 024)

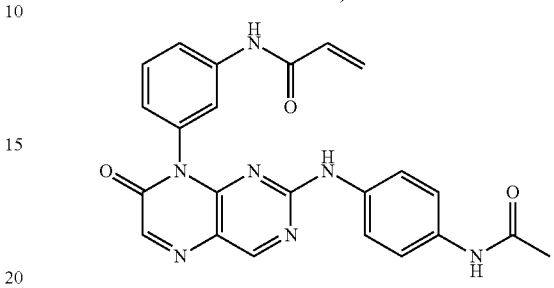

¹H NMR (400 MHz, DMSO-d₆): δ 10.43 (s, 1H), 10.16 (br, 1H), 9.78 (s, 1H), 8.87 (s, 1H), 8.06 (s, 1H), 7.82 (d, J=8.0 Hz, 1H), 7.79 (s, 1H), 7.56 (t, J=8.0 Hz, 1H), 7.32 (br, 2H), 7.23 (br, 2H), 7.15 (d, J=8.0 Hz, 1H), 6.46 (dd, J=17.0, 10.2 Hz, 1H), 6.25 (dd, J=17.0, 1.8 Hz, 1H), 5.76 (dd, J=10.2, 1.8 Hz, 1H), 1.98 (s, 3H). HRMS (ESI) calculated for $C_{23}H_{20}N_7O_3$ [M+H]⁺ 442.1628. found 442.1624.

4-(8-(3-acrylamidephenyl)-7-oxo-7,8-dihydropteridinyl-2-amino)benzamide (Compound 025)

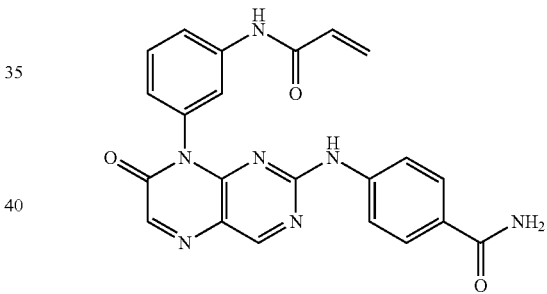

¹H NMR (400 MHz, DMSO-d₆): δ 10.43 (s, 1H), 10.40 (s, 1H), 8.95 (s, 1H), 8.13 (s, 1H), 7.86 (s, 1H), 7.79 (d, J=8.0 Hz, 1H), 7.71 (br, 1H), 7.61 (t, J=8.0 Hz, 1H), 7.55 (d, J=7.6 Hz, 2H), 7.47 (br, 2H), 7.18 (d, J=7.6 Hz, 2H), 6.44 (dd, J=17.0, 10.2 Hz, 1H), 6.25 (dd, J=17.0, 1.8 Hz, 1H), 5.76 (dd, J=10.2, 1.8 Hz, 1H). HRMS (ESI) calculated for $C_{22}H_{18}N_7O_3$ [M+H]⁺ 428.1471. found 428.1476.

N-(3-(2-(4-methoxyphenylamino)-6-methyl-7-oxo-8 (7H)-pteridin-yl)phenyl) acrylamide (Compound 026)

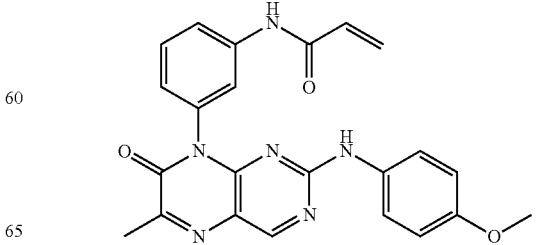

¹H NMR (400 MHz, DMSO-d₆): δ 10.42 (s, 1H), 9.93 (br, 1H), 8.78 (s, 1H), 7.83 (d, J=8.0 Hz, 1H), 7.77 (s, 1H), 7.56 (t, J=8.0 Hz, 1H), 7.31 (br, 2H), 7.11 (d, J=8.0 Hz, 1H), 6.58 (br, 2H), 6.45 (dd, J=17.0, 10.2 Hz, 1H), 6.26 (d, J=17.0 Hz, 1H), 5.77 (d, J=10.2 Hz, 1H), 3.65 (s, 3H), 2.42 (s, 3H). HRMS (ESI) calculated for $C_{23}H_{21}N_6O_3$ [M+H]⁺ 429.1675. found 429.1675.

N-(3-(8-(4-methoxyphenyl)-7-oxo-7,8-dihydro-pteridin-2-amino)phenyl) acrylamide (Compound 027)

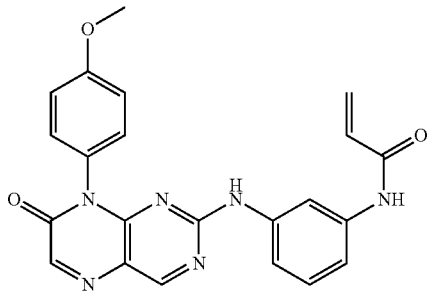 [SMILES: C=CC(=O)Nc1cccc(Nc2ncc3ncc(=O)n(-c4ccc(OC)cc4)c3n2)c1]

¹H NMR (400 MHz, DMSO-d₆): δ 10.17 (s, 1H), 10.01 (s, 1H), 8.89 (s, 1H), 8.07 (s, 1H), 7.63 (br, 1H), 7.33 (d, J=8.8 Hz, 2H), 7.27 (d, J=8.0 Hz, 1H), 7.23 (d, J=8.0 Hz, 1H), 7.11 (d, J=8.8 Hz, 2H), 6.89 (br, 1H), 6.46 (dd, J=17.0, 10.2 Hz, 1H), 6.25 (dd, J=17.0, 1.8 Hz, 1H), 5.74 (dd, J=10.2, 1.8 Hz, 1H), 3.85 (s, 3H). HRMS (ESI) calculated for $C_{22}H_{19}N_6O_3$ [M+H]⁺ 415.1519. found 415.1519.

2-(3-aminophenylamino)-8-(4-methoxyphenyl)-7(8H)-pteridin-one (Compound 028)

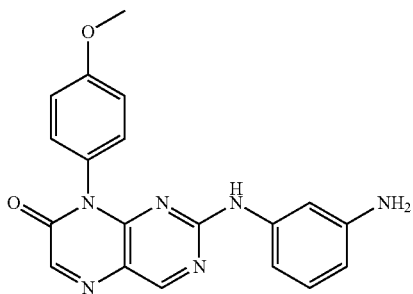 [SMILES: COc1ccc(-n2c(=O)cnc3cnc(Nc4cccc(N)c4)nc32)cc1]

¹H NMR (400 MHz, DMSO-d₆): δ 9.91 (s, 1H), 8.85 (s, 1H), 8.04 (s, 1H), 7.35 (d, J=8.8 Hz, 2H), 7.16 (d, J=8.8 Hz, 2H), 6.68-6.65 (m, 3H), 6.16 (d, J=7.2 Hz, 1H), 4.63 (s, 2H), 3.86 (s, 3H). HRMS (ESI) calculated for $C_{19}H_{17}N_6O_2$ [M+H]⁺ 361.1413. found 361.1411.

N-(4-(8-(4-methoxyphenyl)-7-oxo-7,8-dihydro-pteridin-2-amino)phenyl) acrylamide (Compound 029)

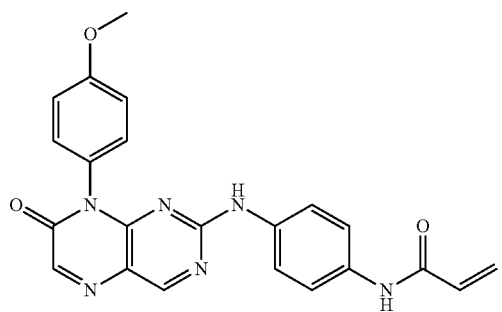 [SMILES: C=CC(=O)Nc1ccc(Nc2ncc3ncc(=O)n(-c4ccc(OC)cc4)c3n2)cc1]

¹H NMR (400 MHz, DMSO-d₆): δ 10.19 (br, 1H), 10.03 (s, 1H), 8.87 (s, 1H), 8.05 (s, 1H), 7.36-7.34 (m, 6H), 7.16 (d, J=8.4 Hz, 2H), 6.41 (dd, J=17.0, 10.2 Hz, 1H), 6.23 (dd, J=17.0, 1.6 Hz, 1H), 5.72 (dd, J=10.2, 1.6 Hz, 1H), 3.92 (s, 1H). HRMS (ESI) calculated for $C_{22}H_{19}N_6O_3$ [M+H]⁺ 415.1519. found 415.1524.

2-(4-aminophenylamino)-8-(4-methoxyphenyl)-7(8H)-pteridin-one (Compound 030)

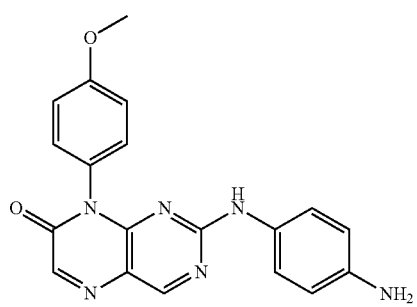 [SMILES: COc1ccc(-n2c(=O)cnc3cnc(Nc4ccc(N)cc4)nc32)cc1]

¹H NMR (400 MHz, DMSO-d₆): δ 9.87 (s, 1H), 8.77 (s, 1H), 7.97 (s, 1H), 7.32 (d, J=8.8 Hz, 2H), 7.13 (d, J=8.8 Hz, 2H), 7.08 (br, 2H), 6.24 (br, 2H), 4.84 (s, 2H), 3.88 (s, 3H). HRMS (ESI) calculated for $C_{19}H_{17}N_6O_2$ [M+H]⁺ 361.1413. found 361.1417.

N-(4-(2-(2-methoxy)-4-(4-methoxy-1-piperazinyl)-phenylamino)-7-oxo-8(7H)-pteridinyl)phenyl)acrylamide (Compound 031)

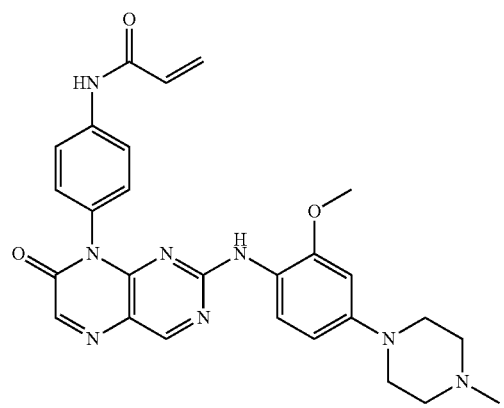 [SMILES: C=CC(=O)Nc1ccc(-n2c(=O)cnc3cnc(Nc4ccc(N5CCN(C)CC5)cc4OC)nc32)cc1]

¹H NMR (400 MHz, DMSO-d₆): δ 10.43 (s, 1H), 8.80 (s, 1H), 8.42 (s, 1H), 8.03 (s, 1H), 7.85 (d, J=8.6 Hz, 2H), 7.34 (d, J=8.6 Hz, 2H), 7.25 (d, J=8.8 Hz, 1H), 6.54-6.48 (m, 2H), 6.33 (dd, J=17.0, 1.6 Hz, 1H), 6.02 (br, 1H), 5.84 (dd, J=10.2, 1.6 Hz, 1H), 3.76 (s, 3H), 3.02 (br, 4H), 2.43 (br, 4H), 2.23 (s, 3H). HRMS (ESI) calculated for $C_{27}H_{29}N_8O_3$ [M+H]⁺ 513.2363. found 513.2362.

N-(3-(2-(2-methoxy-4-(4-methyl-1-piperazinyl)-phenylamino)-7-oxo-8(7H)-pteridin-yl)phenyl)acrylamide (Compound 032)

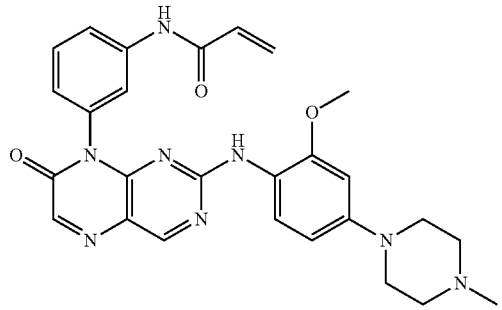 [SMILES: C=CC(=O)Nc1cccc(-n2c(=O)cnc3cnc(Nc4ccc(N5CCN(C)CC5)cc4OC)nc32)c1]

$^1$H NMR (400 MHz, DMSO d$_6$): δ 10.41 (s, 1H), 8.80 (s, 1H), 8.44 (br, 1H), 8.02 (s, 1H), 7.86 (br, 1H), 7.71 (s, 1H), 7.52 (t, J=8.0 Hz, 1H), 7.30 (d, J=7.6 Hz, 1H), 7.09 (d, J=8.0 Hz, 1H), 6.53 (s, 1H), 6.46 (dd, J=17.0, 10.2 Hz, 1H), 6.26 (dd, J=17.0, 1.8 Hz, 1H), 6.02 (br, 1H), 5.78 (dd, J=10.2, 1.8 Hz, 1H), 3.76 (s, 3H), 3.04 (br, 4H), 2.44 (br, 4H), 2.23 (s, 3H). HRMS (ESI) Calculated for C$_{27}$H$_{29}$N$_8$O$_3$ [M+H]$^+$ 513.2363. Found 513.2361.

EXAMPLE 2

Assay on Bioactivity—1

Inhibitory effects in vitro of the compounds provided in the present invention on EGFR kinase activity was tested as follows:

In vitro enzyme activity assay: wild-type and various mutants (T790M, L858R, L861Q, L858 R/T790M) EGFR, Z'-Lyte Kinase Assay Kit were purchased from Invitrogen. 10 concentration gradients, from $5.1 \times 10^{-11}$ mol/L to $1.0 \times 10^{-6}$ mol/L, were set for all of the compounds to be tested.

Concentrations of different kinases were determined based on the optimization of experiment, and the corresponding concentrations were: EGFR (PV3872, Invitrogen) 0.287 μg/μL, EGFR-T790M (PV4803, Invitrogen) 0.174 μg/μL, EGFR-L858R (PV4128, Invitrogen) 0.054 μg/μL, EGFR-L858R/T790M (PV4879, Invitrogen) 0.055 μg/μL.

Compounds were diluted for 3 times in DMSO from $5.1 \times 10^{-9}$ M to $1 \times 10^{-4}$ M. 4 μL of compound was dissolved in 96 μL of water, to give a 4× compound solution. 40 μM ATP was dissolved in 1.33× kinase buffer, and a kinase/peptide mixture comprising 2× kinase, 4 μM tyrosine and four peptides was prepared for use. 10 μL of kinase reaction system comprised 2.5 μL of compound solution, 5 μL of Kinase/peptide mixture, and 2.5 μL of ATP solution. 5 μL of phosphopeptide solution was used in place of kinase/peptide mixture as 100% phosphorylation control. 2.5 μL of 1.33× kinase buffer was used to replace ATP solution as 100% inhibition control, and 2.5 μL of 4% DMSO solution was used to replace compound solution as 0% inhibition control. After thoroughly mixing the solution within the plate, the plate was incubated at room temperature for 1.5 hours. 5 μL of DevelopmentSolution was added into each well, and then the plate was incubated at room temperature for another 1 hour, and non-phosphorylated peptide was cleaved within this period. Finally, the reaction was quenched by adding 5 μL of Stop Reagent. The Plate was measured with EnVision Multilabel Reader (Perkin Elmer). Experimental data were calculated by using GraphPad Prism version 4.0. Each experiment was repeated more than three times.

The test results are shown in Table 1.

TABLE 1

| Compound No. | Inhibitory activity on EGFR kinase (IC$_{50}$, nM) | | | |
| --- | --- | --- | --- | --- |
| | T790M | WT | L858R | T790M/L858R |
| 001 | >10000 | >10000 | >10000 | >10000 |
| 002 | 665 | 446 | 546 | 606 |
| 003 | 8698 | 8011 | 4082 | 3297 |
| 004 | >10000 | 3181 | 4877 | >10000 |
| 005 | >10000 | >10000 | 87159 | >10000 |
| 006 | 19.4 | 10.6 | 10.1 | 8.4 |
| 007 | >10000 | >10000 | >10000 | >10000 |
| 008 | >10000 | >10000 | >10000 | >10000 |
| 009 | 10.9 | 60.7 | 81.11 | 39.1 |
| 010 | 2253 | 8086 | 6084 | 2022 |
| 011 | | 67 | 84.8 | 70.3 |
| 012 | | 5980 | 5342 | 1920 |
| 013 | | 86.6 | 101 | 39.5 |
| 014 | | 16.1 | 26.4 | 113.2 |
| 015 | | 14.7 | 12.4 | 5.28 |
| 016 | | 7580 | 115.9 | 1491 |
| 017 | | 67 | 84.8 | 70.3 |
| 018 | | 7.94 | 5.83 | 3.02 |
| 019 | | 1260 | 6382 | 738 |
| 020 | | 1.47 | 1.2 | 0.824 |
| 021 | | 19.7 | 11.7 | 5.49 |
| 022 | | 23.3 | 12.6 | 5.33 |
| 023 | | 23.1 | 16.3 | 5.57 |
| 024 | | 15.8 | 13.4 | 5.12 |
| 025 | | 12.7 | 9.64 | 4.39 |
| 026 | | 7.24 | 5.93 | 16 |
| 027 | | 2000 | 1710 | 1200 |
| 028 | | 10603 | 18881 | 3534 |
| 029 | | >10000 | 1318 | >10000 |
| 030 | | 3415 | 23758 | 6751 |
| 031 | | 429 | 376 | 229 |
| 032 | | 3.67 | 2.36 | 1.17 |
| WZ4002 | | 9.58 | 2.6 | 1.02 |

Assay on Bioactivity—2

Cell proliferation and growth inhibition analysis: H1975 (non-small cell lung cancer cells, EGFR$^{L858/T790M}$), HCC827 (non-small cell lung cancer cells, EGFR$^{del\ E746-A750}$), A549 (non-small cell lung cancer cells, EGFR wild-type), BT474 (breast cancer cells, Her2 overexpression), SK-BR-3 (breast cancer cells, Her2 overexpression), MCF-7 (breast cancer cells, Her2 overexpression) cells were obtained from ATCC. Cell proliferation was evaluated by MTS assay. Cells were exposed to the process conditions for 72 hours, and the number of cells for each cell line used in the experiment was adjusted according to the absorbance value (absorbance value at 490 nm was 1.3-2.2). 6 concentration gradients (0.1 nM-10 μM) were set for the compounds to be tested, with six parallel controls for each concentration.

H1975, HCC827, A549, BT474, MCF-7, SK-BR-3 cells were cultured in the corresponding medium. Upon recovery, the cells were passaged at least two times and then used in experiments. Cells in Log phase were trypsinized and resuspended in the medium. H1975 (1000 cells per well), BT474 (1500 cells per well), MCF-7 (1500 cells per well), HCC827 (2000 cells per well), SK-BR-3 (2000 cells per well), A549 (2000 cells per well) were seeded into 96-well plates, the volume was 100 μL, and 6 rows and 7 columns were set. The plate was placed in an incubator at 37° C. of 5% carbon dioxide overnight. Compounds were dissolved in DMSO to obtain the concentration of 10 μM, and then gradually diluted to obtain the concentration of compound as 10 μM, 0.1 μM, 0.01 μM, 0.001 μM, 0.0001 μM. 2 μL of compound solution was added into 998 μL of medium, and the resulting mixture was thoroughly mixed. 100 μL of mixture was added into 96-well plate. 2 μL of DMSO was used to replace the compound solution as 0% inhibition control. After the cells were cultured for 68 hours, 20 μL of MTT (5 mg/mL) was added. After 4 hours, the supernatant was discarded and 150 μL of DMSO was added. The resulting system was shaken for 10 minutes, and the plate was read with Synergy HT (Bio TeK) (OD490). The data was calculated by Graph-Pad Prism version 4.0, and $IC_{50}$ was obtained by non-linear regression model using dose-response curve.

The test results are shown in Table 2 and 3.

TABLE 2

| Compound No. | Inhibitory activity on cell proliferation ($IC_{50}$, μM) | |
|---|---|---|
| | HCC827 | H1975 |
| 001 | >10 | >10 |
| 002 | 1.29 | 2.75 |
| 003 | 3.01 | >10 |
| 004 | 3.33 | >10 |
| 005 | >10 | >10 |
| 006 | 0.009 | 0.133 |
| 007 | >10 | >10 |
| 008 | >10 | >10 |
| 009 | 0.91 | 4.65 |
| 010 | 4.16 | >10 |
| 011 | 2.29 | 5.6 |
| 012 | 4.42 | 18.9 |
| 013 | 0.914 | 3.51 |
| 014 | 68.1 | 77.8 |
| 015 | 0.015 | 0.437 |
| 016 | 68.7 | 20.8 |
| 017 | 0.163 | 0.82 |
| 018 | 0.017 | 0.216 |
| 019 | 0.676 | 8.87 |
| 020 | 0.002 | 0.043 |
| 021 | 0.02 | 0.238 |
| 022 | 0.073 | 0.531 |
| 023 | 0.031 | 0.477 |
| 024 | 0.229 | 6.08 |
| 025 | 0.604 | 7.3 |
| 026 | 0.013 | 1.22 |
| 027 | 0.408 | 3.05 |
| 028 | 15.9 | 82.8 |
| 029 | 0.543 | 0.953 |
| 030 | 4.65 | 15.3 |
| 031 | 0.466 | 2.88 |
| 032 | 0.004 | 0.038 |
| WZ4002 | 0.014 | 0.039 |
| Iressa | 0.006 | 13 |

TABLE 3

| Compound No. | Inhibitory activity on cell proliferation ($IC_{50}$, μM) | | | |
|---|---|---|---|---|
| | A549 | SK-BR-3 | MCF-7 | BT474 |
| 001 | >10 | >10 | >10 | >10 |
| 002 | 1.23 | 1.57 | 1.51 | >10 |
| 003 | >10 | >10 | >10 | >10 |
| 004 | >10 | >10 | >10 | >10 |
| 005 | >10 | >10 | >10 | >10 |
| 006 | 0.73 | 2.35 | 15.0 | 2.24 |
| 007 | >10 | >10 | >10 | >10 |
| 008 | 6.12 | >10 | >10 | >10 |
| 009 | 2.24 | 1.15 | 2.41 | 0.84 |
| 010 | >10 | 7.17 | 3.60 | 3.43 |

Assay on Bioactivity—3

Kinase selectivity analysis: kinase selectivity experiment was performed by Shanghai ChemPartner using Caliper assay screening platform. All of kinases and other materials were purchased from commercial companies. Staurosporine and PI103 were used as control compounds in testing inhibitory activity of compound on different kinases.

I. Mobility Shift Assay

1. Preparation of kinase matrix buffer and stop buffer for kinase test: 1) 1× kinase matrix buffer: 50 mM HEPES pH 7.5, 0.0015% Brij-35, 10 mM MgCl2, 2 mM DTT; 2) stop buffer: 100 mM HEPES, pH 7.5, 0.015% Brij-35, 0.2% Coating Reagent #3, 50 mM EDTA.

2. Preparation of compound solution: 1) the compound was diluted in 100% DMSO to a concentration, which was 50 times of the highest concentration used in test, and 100 μL of the compound solution as said above was placed into each well of 96-well plate. 2) 30 μL of compound solution was transferred into 60 μL of 100% DMSO in the adjacent well, and the above operation was repeated for sequentially diluting the compound. 3) 100 μL of 100% DMSO was added into two blank wells as no-compound and no-enzyme control, and the plate was marked as stock solution plate. 4) 10 μL of solution from the stock solution plate was added into another 96-well plate as a temporary plate, and into each well, 90 μL of 1× kinase buffer was added, the temporary plate was placed on a shaker for uniformly mixing the compound solution.

3. Preparation of assay plate: 5 μL of solution from each well of the 96-well temporary plate was added into a 384-well plate, and the experiment was independently repeated.

4. Kinase reaction: 1) preparation of 2.5× enzyme solution by adding the kinase into 1× kinase matrix buffer. 2) preparation of 2.5× peptide solution: FAM labeled peptide, and ATP were added into 1× kinase matrix buffer. 3) 2.5× enzyme solution was transferred into the assay plate. 4) the assay plate comprised 5 μL of the compound solution in 10% DMSO. 5) 10 μL of 2.5× enzyme solution was added into each well of the 384-well assay plate. 6) The assay plate was incubated at room temperature for 10 minutes. 7) 2.5× peptide solution was transferred to the assay plate, and 10 μL of peptide solution was added into each well of the 384-well assay plate. 8) kinase reaction and termination: after incubated at 28° C. for a certain time, 25 μL of stop buffer was added to quench the reaction.

5. Caliper readings: experimental data were collected on Caliper.

6. Curve fitting: 1) conversion data were replicated from Caliper program. 2) the conversion value was converted into inhibition rate, inhibition rate %=(maximum−conversion value)/(maximum−minimum)*100, wherein "maximum" represents DMSO control, and minimum represents the low control.

II. Kinase-Glo Analysis

1. Preparation of 1× kinase buffer for PI3Ka kinase test: 1× kinase buffer: 50 mM HEPES, pH 7.5, 3 mM $MgCl_2$, 1 mM EGTA, 100 mM NaCl, 0.03% CHAPS, 2 mM DTT.

2. Preparation of compounds for PI3Ka kinase test: 1) serial dilution of compound and preparation of stock solution plate. The compound was diluted in 100% DMSO to a concentration, which was 100 times of the highest concentration used in reaction, and 100 μL of the compound solution as said above was transferred into each well of 96-well plate. 30 μL of compound solution was transferred into 60 μL of 100% DMSO in the adjacent well, and the above operation was repeated for sequentially diluting the compound. 100 μL of 100% DMSO was added into two blank wells as no-compound and no-enzyme control, the plate was marked as stock solution plate. 2) Preparation of temporary plate. 4 μL of solution from the stock solution plate was transferred to another 96-well plate, 96 μL of 1× kinase buffer was added into each well, and the temporary plate was placed on a shaker and shaken for 10 mins for uniformly mixing the compound solution. 3) Preparation of assay plate. 2.5 μL of solution from each well of the 96-well temporary plate was added into a 384-well plate, and the experiment was independently repeated.

3. Kinase PI3Ka reaction: 1) Preparation of 4× kinase solution. PI3Ka solution was prepared in 1× kinase buffer, the concentration of which was 4 times of the final concentration in the test. 2.5 μL of 1× kinase solution was added into each well of the assay plate (except for control well, into which 2.5 μL of kinase buffer was added), and the assay plate was shaken. 2) Preparation of 2× substrate solution. PIP2 substrate, ATP solution was prepared in 1× kinase reaction buffer, the concentration of which was 2 times of the final concentration in the test. 5 μL of substrate solution was added into each well of the assay plate and shaken to evenly mix contents. 3) The kinase reaction was conducted by incubating at room temperature for 1 hour.

4. Kinase assay. Kinase-Glo Reagent was balanced to r.t., and 10 μL of Kinase-Glo reagent was added into the assay plate to quench the reaction. Upon simple mixing, the plate was centrifuged, and slowly shaken on an oscillator for 15 minutes, and then data was read on a luminescence reader.

5. The data were read and collected on Flexstation.

6. Curve fitting: RLU data were replicated from Flexstation program. The data were converted into inhibition rate % Inhibition rate %=(RLU of sample−minimum)/(maximum−minimum)*100, wherein "maximum" represents the RLU data of no-enzyme control, and "minimum" represents the RLU value of DMSO control group.

III. BRAF Analysis

1. Preparation of 1× Kinase Buffer: 50 mM HEPES, pH 7.5, 10 mM MgCl$_2$, 1 mM EGTA, 0.01% BRIJ-35.

2. Preparation of compounds for BRAF kinase test: 1) serial dilution of compound and preparation of stock solution plate. The compound was diluted in 100% DMSO to a concentration, which was 100 times of the highest concentration used in reaction, and 100 μL of the compound solution as said above was transferred into wells of 96-well plate. 30 μL of compound solution was transferred into 60 μL of 100% DMSO in the adjacent well, and the above operation was repeated for sequentially diluting the compound. 100 μL of 100% DMSO was added into two blank wells as no-compound and no-enzyme control, the plate was marked as stock solution plate. 2) Preparation of temporary plate. 4 μL of compound solution from the stock solution plate was transferred to another 96-well plate, 96 μL of 1× kinase buffer was added into each well, and the temporary plate was placed on a shaker and shaken for 10 mins for uniformly mixing the compound solution. 3) Preparation of assay plate. 2.5 μL of solution from each well of the 96-well temporary plate was added into a 384-well plate, and the experiment was independently repeated.

3. Kinase BRAF reaction: 1) Preparation of 2× kinase solution. BRAF solution was prepared in 1× kinase buffer, the concentration of which was 2 times of the final concentration in the test. 5 μL of kinase solution was added into each well of the assay plate (except for control well, into which 5 μL of 1× kinase buffer was added), and the assay plate was shaken. 2) Preparation of 4× substrate solution. Fluorescein-MAP2K1, ATP substrate solution was prepared in 1× kinase buffer, the concentration of which was 4 times of the final concentration in the test. 2.5 μL of substrate solution was added into each well of the assay plate to start the reaction, and the assay plate was shaken. 3) The kinase reaction was conducted by incubating at room temperature for 1 hour.

4. Kinase assay. Test solution was prepared in antibody dilution buffer, the concentration of which was 2 times of the following final concentration: antibody 2 nM, EDTA 10 μM. 10 μL of test solution was added into each well of the assay plate to quench the assay. Upon simple mixing, the plate was centrifuged, and incubated for at least 30 mins.

5. Read data: the data was read on Envision (excitation at 340 nM, emission at 520 nM, 495 nM).

6. Curve fitting: RLU data were replicated from Envision program. The rate of RFU 520 nM/495 nM was calculated and converted into inhibition rate % Inhibition rate %=(maximum−rate of sample)/(maximum−minimum)*100, wherein "maximum" represents DMSO control rate, and "minimum" represents the no-enzyme control rate. Curve fitting was performed through XLFit excel add-in version 4.3.1.

Test results are shown in the following table.

TABLE 4

| Kinase | % inhibition (10 μM) | | % inhibition (1 μM) | |
|---|---|---|---|---|
| | Compound 020 | Compound 032 | Compound 020 | Compound 032 |
| HER2 | 98 | 100 | 97 | 89 |
| HER4 | 72 | 77 | 60 | 60 |
| FLT1 | 58 | 11 | 17 | 9.4 |
| FLT3 | 99 | 91 | 82 | 60 |
| CDK2 | 49 | 48 | 18 | 25 |
| BLK | 100 | 99 | 99 | 85 |
| JAK2 | 36 | 22 | 22 | 9.9 |
| LCK | 73 | 54 | 18 | 14 |
| LYNA | 40 | 20 | 11 | 6.1 |
| cKit | −3.2 | −4.8 | −12 | −9.3 |
| PIM1 | 54 | 8.9 | 8.2 | 2.1 |
| FGFR3 | 33 | 13 | 14 | 11 |
| FGFR1 | 63 | 42 | 19 | 7.9 |
| PDGFRa | 35 | 18 | 4.9 | 1.2 |
| PDGFRb | 84 | 61 | 42 | 14 |
| KDR | 73 | 29 | 25 | 3.8 |
| SRC | 72 | 33 | 27 | 6.6 |
| ABL | 39 | 13 | 11 | 5.8 |
| AUR B | 87 | 69 | 52 | 32 |
| C-MET | 53 | 28 | 27 | 13 |
| BRAF | 21 | −5.2 | −7.0 | 0.35 |
| PKACa | 4.7 | 4.0 | 15 | 6.9 |
| IKKB | 2.0 | −4.3 | 9.4 | −3.3 |
| IGF1R | 36 | 37 | 21 | 15 |
| GSK3b | 34 | 16 | 16 | 12 |
| P38a | 21 | 1.2 | 2.8 | −5.6 |
| ERK1 | 19 | −4.0 | 1.3 | 11 |

Assay on Bioactivity—4

Inhibitory effects in vitro of the compounds provided in the present invention on BLK and FLT3 kinase activity was tested as follows, wherein BLK, FLT3 were purchased from BPS, and staurosporine was used as a control compound:

Preparation of 1× kinase matrix buffer and stop buffer. 1× kinase matrix buffer: 50 mM HEPES, pH 7.5, 0.0015% Brij-35, 10 mM MgCl$_2$, 2 mM DTT; stop buffer: 100 mM HEPES, pH 7.5, 0.0015% Brij-35, 0.2% Coating Reagent #3, 50 mM EDTA.

Preparation of compound solution. The compound was dissolved in 100% DMSO to a concentration, which was 50 times of the final highest inhibiting-concentration. 100 μL of the compound solution as said above was transferred into wells of 96-well plate. The above compound solution was sequentially diluted to the final desired concentration. In two blank wells of same 96-well plate, 100 μL of 100% DMSO was added as no-compound and no-kinase control, and this plate was used as the original plate.

Preparation of intermediate plate. 10 μL of compound solution was transferred from the original plate to another 96-well plate as the intermediate plate; 90 μL of 1× kinase buffer was added into each well of the intermediate plate, and the intermediate plate was shaken for 10 min.

Preparation of assay plate. 5 μL of solution from each well of intermediate plate was added into a 384-well plate, and repeated controls were set.

Kinase reaction. 2.5× kinase solution and 2.5× peptide solution were prepared. 2.5× kinase solution was transferred into assay plate. Assay plate comprised 5 μL of the compound solution in 10% DMSO. 10 μL of 2.5× kinase solution was added in each well of 384-well assay plate. The plate was incubated at room temperature for 10 minutes. 2.5× peptide solution was added into each well. After incubated at 28° C. for an appropriate time, 25 μL of stop buffer was added to quench the reaction. Experimental data were collected in Caliper. Curve was fitted. Experimental data were copied from Caliper program, and converted into inhibit rate Inhibition %=(Max−Conversion)/(Max−Min)*100, wherein "Max" represents DMSO control, "Min" represents a lower control.

Test results are shown in the following table 5.

TABLE 5

| | Inhibitory activity on kinase ($IC_{50}$, nM) | |
|---|---|---|
| Compound | BLK | FLT3 |
| 001 | >10000 | 27 |
| 002 | 3037 | 128 |
| 003 | 4168 | 137 |
| 004 | >10000 | 206 |
| 005 | >10000 | 30 |
| 006 | 69 | 1591 |
| 007 | >10000 | 1486 |
| 008 | >10000 | 115 |
| 009 | 5312 | 152 |
| 010 | 106 | 4387 |
| 011 | 89 | 48 |
| 012 | 6321 | 160 |
| 013 | 171 | 3778 |
| 014 | 7479 | 129 |
| 015 | 124 | 1859 |
| 016 | >10000 | 358 |
| 017 | 156 | 2825 |
| 018 | 41 | 798 |
| 019 | 796 | 51 |
| 020 | <14 | 322 |
| 021 | 83 | 878 |
| 022 | 98 | 1084 |
| 023 | 83 | 1757 |
| 024 | 148 | 3548 |
| 025 | 76 | 1791 |
| 026 | 96 | 568 |
| 027 | 5656 | 119 |
| 028 | 7946 | 34 |
| 029 | >10000 | 100 |
| 030 | >10000 | 43 |
| 031 | 812 | 180 |
| 032 | 463 | 1169 |
| Staurosporine | 5.6 | 0.28 |

The present invention is illustrated by the specific examples. However, it is appreciated that the scope of the invention should not be limited to these specific examples, while are defined in the claims. And any equivalent modification to the invention should fall within the scope of the invention.

The invention claimed is:
1. A compound having the structure of Formula II:

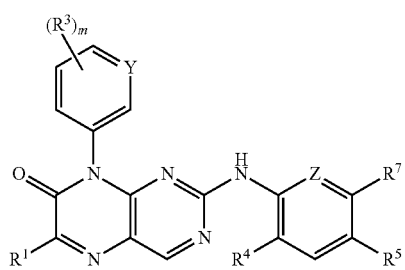

wherein
Y is selected from N, CH;
Z is selected from N, $CR^6$;
$R^1$ is a hydrogen, a halogen, a $C_1$-$C_6$ alkoxyl, an optionally substituted $C_1$-$C_6$ alkyl, an optionally substituted aryl, or an optionally substituted aralkyl;
each of $R^3$ is independently selected from a halogen, a hydroxy, an optionally substituted acyloxy, an amino, an optionally substituted acylamino, an optionally substituted $C_1$-$C_6$ alkyl, CN, a carbamoyl, a carboxyl, an optionally substituted alkoxyformyl, an optionally substituted phenyl, an optionally substituted N-alkylpiperazinyl, an optionally substituted morpholinyl, an optionally substituted piperidinyl, an optionally substituted pyrrolyl, an optionally substituted pyrrolidinyl, —$NR_aR_b$, or an optionally substituted pyridyl;
each of $R^4$, $R^5$, $R^6$ and $R^7$ is independently selected from a hydrogen, a halogen, a $C_1$-$C_6$ alkoxyl, a hydroxyl, an optionally substituted acyloxy, an amino, an optionally substituted acylamino, an optionally substituted $C_1$-$C_6$ alkyl, CN, a carbamoyl, a carboxyl, an optionally substituted alkoxyformyl, an optionally substituted phenyl, an optionally substituted N-alkylpiperazinyl, an optionally substituted morpholinyl, an optionally substituted piperidinyl, an optionally substituted pyrrolyl, an optionally substituted pyrrolidinyl, —$NR_aR_b$, an optionally substituted pyridyl;
each of $R_a$ and $R_b$ are independently selected from an alkyl and an alkenyl; and
each of m and n is 0, 1, 2, 3 or 4;
wherein "optionally substituted" means that the group modified by the term can be optionally substituted by 1-5 substituents selected from: a halogen, a ($C_{1-3}$ alkyl)-CHO or —CHO, a $C_{1-6}$ straight chain or branched chain alkyl, a cyano, a nitro, an amino, a hydroxyl, a hydroxymethyl, a halogen-substituted alkyl, a halogen-substituted alkoxyl, a carboxyl, a $C_{1-4}$ alkoxyl, an ethoxyformyl, $N(CH_3)$ and a $C_{1-4}$ acyl;
acyloxy refers to a group having the structure of the formula —O—C(O)—R wherein R is selected from an alky, an alkenyl, and an alkynyl and R can be optionally substituted;
acylamino refers to a group having the structure of the formula —R'—NH—C(O)—R, wherein R' is selected from a bond or an alkyl, and R is selected from the group consisting of an alkyl, an alkenyl, an alkynyl, an $NR_aR_b$-substituted alkyl, an $NR_aR_b$-substituted alkenyl, an $NR_aR_b$-substituted alkynyl, a halogen-substituted alkyl, a cyano-substituted alkenyl,

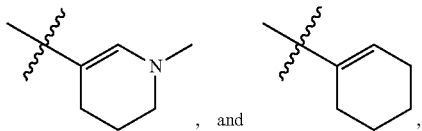

, and , wherein $R_a$ and $R_b$ are selected from an alkyl and an alkenyl.

2. The compound of claim 1, wherein the compound has the structure of formula III:

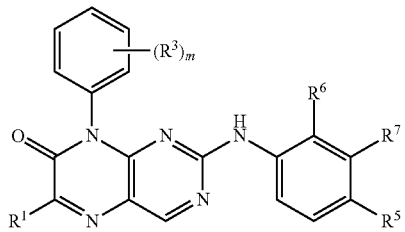

III wherein,
- $R^1$ is a hydrogen, a halogen, a $C_1$-$C_6$ alkoxyl, an optionally substituted $C_1$-$C_6$ alkyl, an optionally substituted aryl, or an optionally substituted aralkyl;
- $R^3$ is independently selected from a halogen, a hydroxyl, an optionally substituted acyloxy, an amino, an optionally substituted acylamino, an optionally substituted $C_1$-$C_6$ alkyl, CN, a carbamoyl, a carboxyl, an optionally substituted alkoxyformyl, an optionally substituted phenyl, an optionally substituted N-alkylpiperazinyl, an optionally substituted morpholinyl, an optionally substituted piperidinyl, an optionally substituted pyrrolyl, an optionally substituted pyrrolidinyl, —$NR_aR_b$, or an optionally substituted pyridyl;
- each of $R^5$, $R^6$ and $R^7$ is independently selected from a hydrogen, a halogen, a $C_1$-$C_6$ alkoxyl, a hydroxyl, an optionally substituted acyloxy, an amino, an optionally substituted acylamino, an optionally substituted $C_1$-$C_6$ alkyl, CN, a carbamoyl, a carboxyl, an optionally substituted alkoxyformyl, an optionally substituted phenyl, an optionally substituted N-alkyl-piperazinyl, an optionally substituted morpholinyl, an optionally substituted piperidinyl, an optionally substituted pyrrolyl, an optionally substituted pyrrolidinyl, —$NR_aR_b$, or an optionally substituted pyridyl;
- each of $R_a$ and $R_b$ are independently selected from an alkyl and an alkenyl; and
- each of m and n is 0, 1, 2, 3 or 4.

3. The compound of claim 2, wherein
- $R^1$ is selected from H, and a $C_1$-$C_6$ alkyl;
- $R^3$ is selected from an amino, an acyloxy, a halogen, a hydroxyl, an alkyl, CN, a carboxyl, a morpholinyl, a N-alkyl-piperazinyl, a piperidinyl, a pyrrolyl, a pyrrolidinyl, a pyridyl, —$NR_aR_b$, an acylamino, and a carbamoyl, wherein $R_a$ and $R_b$ are selected from an alkyl and an alkenyl;
- $R^5$ is selected from H, an alkoxyl, a morpholinyl, a halogen, a N-alkyl-piperazinyl, a piperidinyl, a pyrrolyl, a pyrrolidinyl, a pyridyl, —$NR_aR_b$, an acylamino, and a carbamoyl, wherein $R_a$ and $R_b$ can be selected from an alkyl and an alkenyl;
- $R^6$ is H; and
- $R^7$ is selected from H or an acylamino.

4. The compound of claim 3, wherein
- $R^5$ is selected from a halogen, a 4-N-methylpiperazinyl, a N-morpholinyl, a N-piperidinyl, a N-pyrrolyl, a N-pyrrolidinyl, a N,N-diethyl-amino, a N,N-dimethylmethylamine group, and 4-pyridyl;
- $R^3$ is selected from the group consisting of:

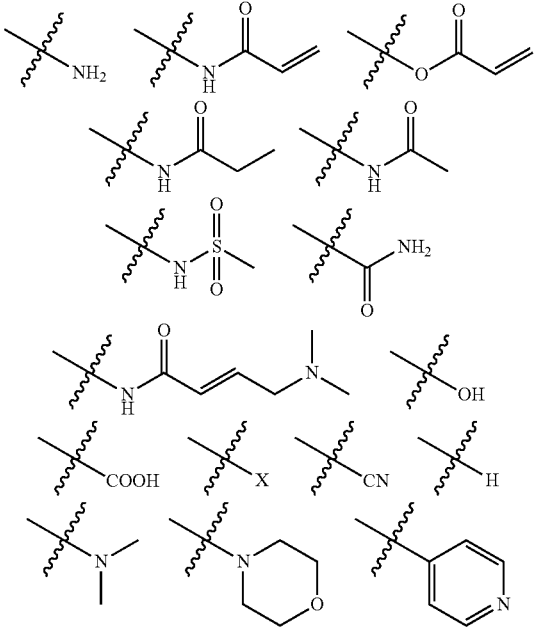

wherein X is a halogen; and
$R^7$ is H.

5. A compound selected from the group consisting of

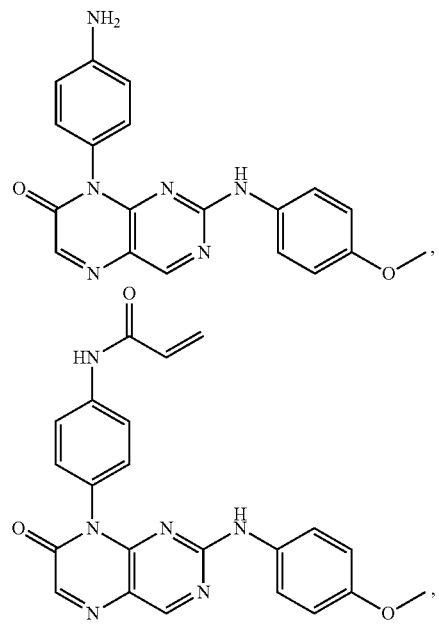

-continued
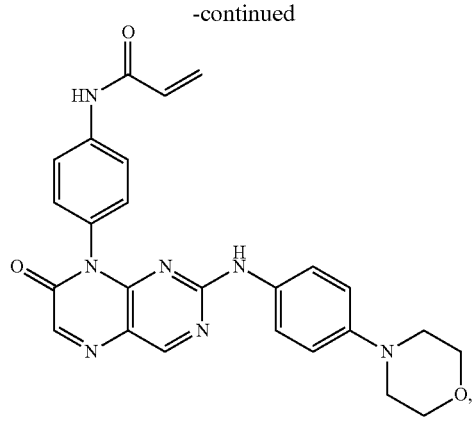
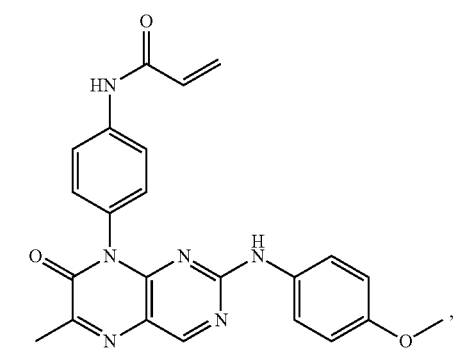
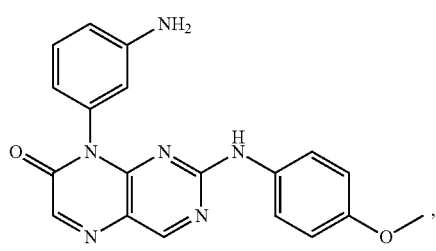
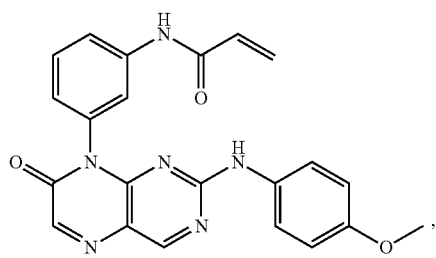
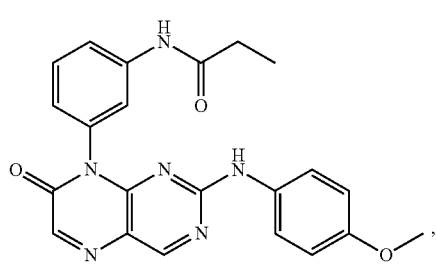
-continued
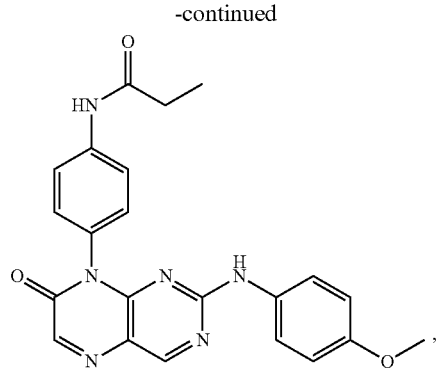
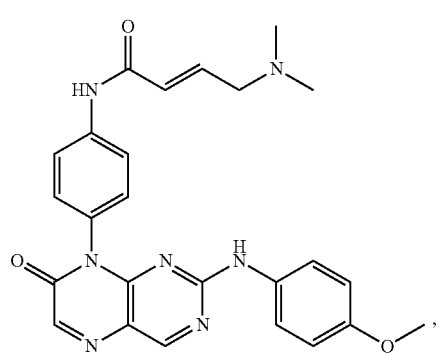
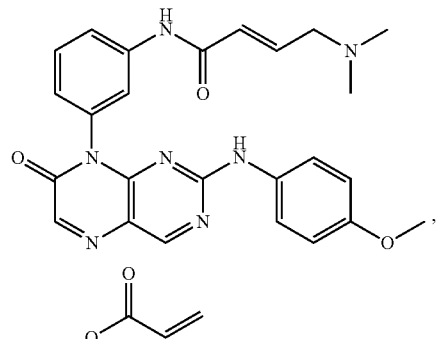
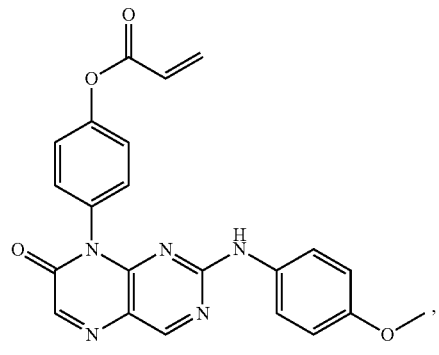
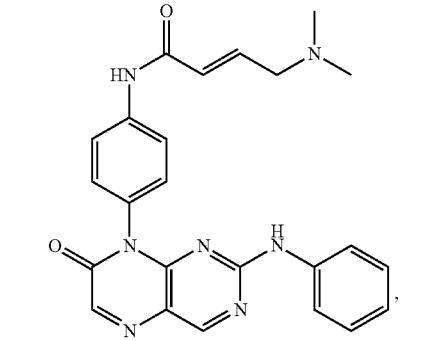

45
46

-continued

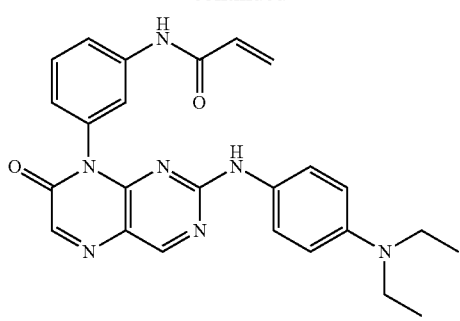

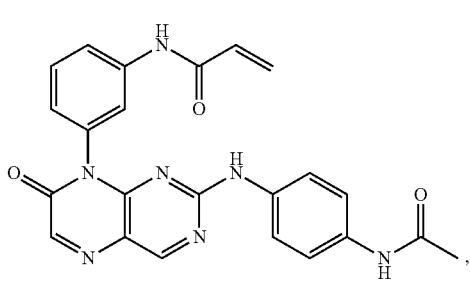

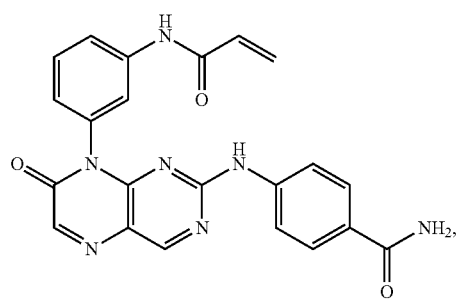

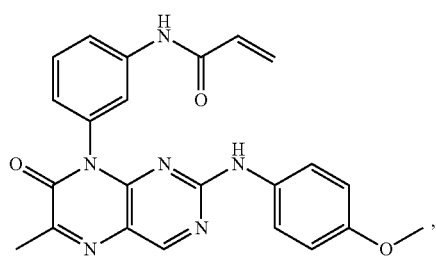

-continued

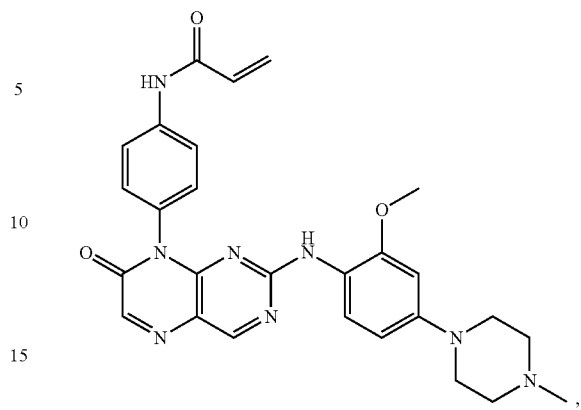

and

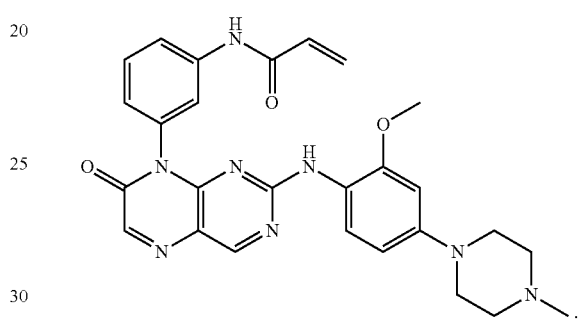

6. A pharmaceutical composition, wherein the pharmaceutical composition comprises the compound of claim 1, or the pharmaceutically acceptable salt thereof, and a pharmaceutically acceptable carrier or excipient.

7. A method of treating lung cancer or breast cancer, said method comprising administering to a subject in need thereof a compound of claim 1.

8. The compound of claim 2, wherein $R^6$ is $OCH_3$.

9. The compound of claim 1, wherein said compound comprises the structure of the formula:

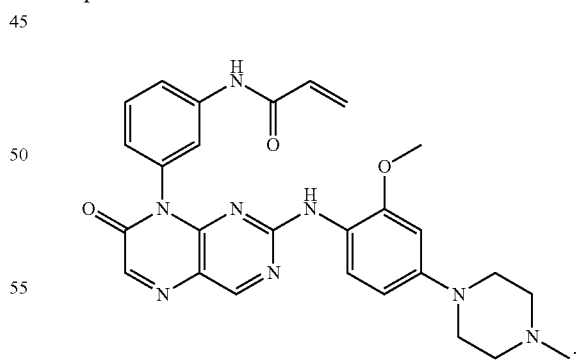

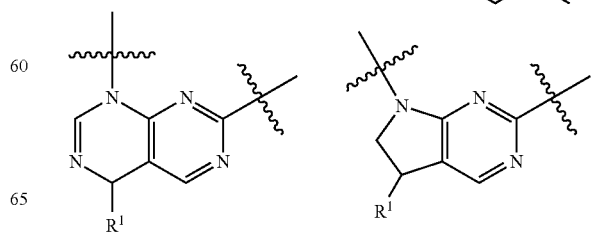

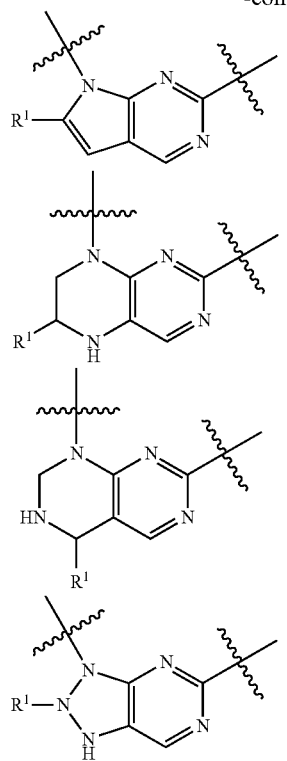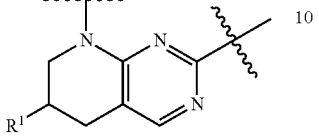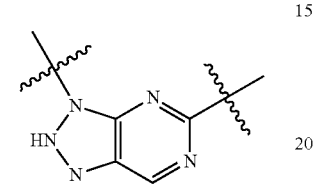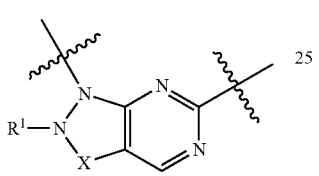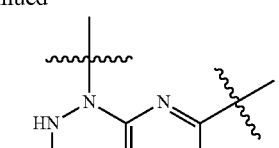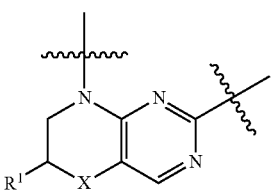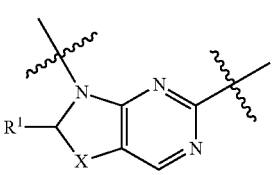
* * * * *